US007335164B2

(12) United States Patent
Mace et al.

(10) Patent No.: US 7,335,164 B2
(45) Date of Patent: Feb. 26, 2008

(54) MULTIPLE FUNCTION AIRWAY ADAPTER

(75) Inventors: Leslie E. Mace, Mercer Island, WA (US); Lawrence L. Labuda, Coupeville, WA (US); Perry R. Blazewicz, Tacoma, WA (US); David R. Rich, Glastonbury, CT (US); Michael B. Jaffe, Cheshire, CT (US); Joseph A. Orr, Park City, UT (US); Scott A. Kofoed, Bountiful, UT (US)

(73) Assignee: NTC Technology, Inc., Murrysville, PA (US)

( * ) Notice: Subject to any disclaimer, the term of this patent is extended or adjusted under 35 U.S.C. 154(b) by 1020 days.

(21) Appl. No.: 09/841,451

(22) Filed: Apr. 24, 2001

(65) Prior Publication Data
US 2002/0029003 A1 Mar. 7, 2002

Related U.S. Application Data

(63) Continuation-in-part of application No. 09/092,260, filed on Jun. 5, 1998, now Pat. No. 6,312,389, which is a continuation-in-part of application No. 08/680,492, filed on Jul. 15, 1996, now Pat. No. 5,789,660, which is a continuation-in-part of application No. 09/128,897, filed on Aug. 4, 1998, now Pat. No. 6,815,211, and a continuation-in-part of application No. 09/128,918, filed on Aug. 4, 1998, now Pat. No. 6,325,978.

(51) Int. Cl.
| A61B 5/08 | (2006.01) |
|---|---|
| G01N 1/22 | (2006.01) |
| G01N 31/00 | (2006.01) |
| G01N 33/497 | (2006.01) |
| B32B 5/02 | (2006.01) |
| B32B 27/94 | (2006.01) |
| B32B 27/12 | (2006.01) |

(52) U.S. Cl. .............. 600/532; 600/538; 73/23.3; 422/84

(58) Field of Classification Search ............. 600/532; 73/23.3; 432/84
See application file for complete search history.

(56) References Cited

U.S. PATENT DOCUMENTS 2,484,217 A    10/1949   Gardenier (Continued)

FOREIGN PATENT DOCUMENTS

DE    196 17 738 C1    6/1997

(Continued)

OTHER PUBLICATIONS

Bacon, J. R., Demas, J. N.; "Determination of Oxygen Concentrations by Luminescence Quenching of a Polymer-Immobilized Transition-Metal Complex;" pp. 2780-2785, *Analytical Chemistry*, vol. 59, No. 23, Dec. 1, 1987.

(Continued)

*Primary Examiner*—Robert L. Nasser
(74) *Attorney, Agent, or Firm*—TraskBritt

(57) ABSTRACT

An integrated airway adapter capable of monitoring any combination of respiratory flow, $O_2$ concentration, and concentrations of one or more of $CO_2$, $N_2O$, and an anesthetic agent in real time, breath by breath. Respiratory flow may be monitored with differential pressure flow meters under diverse inlet conditions through improved sensor configurations which minimize phase lag and dead space within the airway. Molecular oxygen concentration may be monitored by way of luminescence quenching techniques. Infrared absorption techniques may be used to monitor one or more of $CO_2$, $N_2O$, and anesthetic agents.

51 Claims, 15 Drawing Sheets

U.S. PATENT DOCUMENTS

| | | |
|---|---|---|
| 2,706,409 A | 4/1955 | Preston |
| 2,950,237 A | 8/1960 | Sharp et al. |
| 3,410,264 A | 11/1968 | Frederik |
| 3,429,667 A | 2/1969 | Hart et al. |
| 3,449,954 A | 6/1969 | Brown |
| 3,581,565 A | 6/1971 | Dieterich |
| 3,590,473 A | 7/1971 | Carlson |
| 3,612,866 A | 10/1971 | Stevens |
| 3,635,756 A | 1/1972 | Shepard et al. |
| 3,663,833 A | 5/1972 | Pao et al. |
| 3,725,658 A | 4/1973 | Stanley et al. |
| 3,726,271 A | 4/1973 | Mondshine et al. |
| 3,734,691 A | 5/1973 | Kukla et al. |
| 3,734,862 A | 5/1973 | Maulding |
| 3,752,171 A | 8/1973 | Ayre |
| 3,830,222 A | 8/1974 | Chance |
| 3,889,536 A | 6/1975 | Sylvester |
| 3,910,113 A | 10/1975 | Brown |
| 3,937,082 A | 2/1976 | Schilling |
| 3,981,193 A | 9/1976 | Goulet |
| 4,003,707 A | 1/1977 | Lübbers et al. |
| 4,036,054 A | 7/1977 | Goulet |
| 4,047,521 A | 9/1977 | Kramer et al. |
| 4,083,245 A | 4/1978 | Osborn |
| 4,154,100 A | 5/1979 | Harbaugh et al. |
| 4,163,390 A | 8/1979 | Rodder |
| 4,170,134 A | 10/1979 | Nathan |
| 4,223,226 A | 9/1980 | Quick et al. |
| 4,245,507 A | 1/1981 | Samulski |
| 4,272,485 A | 6/1981 | Lübbers |
| 4,321,057 A | 3/1982 | Buckles |
| 4,345,463 A | 8/1982 | Wilson et al. |
| 4,346,584 A | 8/1982 | Boehringer |
| 4,368,740 A * | 1/1983 | Binder ................... 600/532 |
| 4,372,170 A | 2/1983 | Dehart et al. |
| 4,399,099 A | 8/1983 | Buckles |
| 4,403,514 A | 9/1983 | Osborn |
| 4,437,772 A | 3/1984 | Samulski |
| 4,440,177 A * | 4/1984 | Anderson et al. ........... 600/532 |
| 4,476,707 A | 10/1984 | Burns et al. |
| 4,476,870 A | 10/1984 | Peterson et al. |
| 4,481,829 A | 11/1984 | Shortridge |
| RE31,832 E | 2/1985 | Samulski |
| RE31,879 E | 5/1985 | Lübbers et al. |
| 4,542,987 A | 9/1985 | Hirschfeld |
| 4,546,655 A | 10/1985 | Victor |
| 4,568,518 A | 2/1986 | Wolfbeis et al. |
| 4,581,942 A | 4/1986 | Ogura et al. |
| 4,581,945 A | 4/1986 | Rusz |
| 4,587,101 A | 5/1986 | Marsoner et al. |
| 4,608,344 A | 8/1986 | Carter et al. |
| 4,632,807 A | 12/1986 | Marsoner |
| 4,652,143 A | 3/1987 | Wickersheim et al. |
| 4,657,736 A | 4/1987 | Marsoner et al. |
| 4,682,895 A | 7/1987 | Costello |
| 4,730,112 A | 3/1988 | Wong |
| 4,750,837 A | 6/1988 | Gifford et al. |
| 4,752,115 A | 6/1988 | Murray, Jr. et al. |
| 4,775,514 A | 10/1988 | Barnikol et al. |
| 4,784,486 A | 11/1988 | VanWagenen et al. |
| 4,810,655 A | 3/1989 | Khalil et al. |
| 4,822,899 A | 4/1989 | Groves et al. |
| 4,823,615 A | 4/1989 | Taha |
| 4,849,172 A | 7/1989 | Yafuso et al. |
| 4,859,858 A | 8/1989 | Knodle et al. |
| 4,859,859 A | 8/1989 | Knodle et al. |
| 4,861,727 A | 8/1989 | Hauenstein et al. |
| RE33,064 E | 9/1989 | Carter et al. |
| 4,892,383 A | 1/1990 | Klainer et al. |
| 4,892,941 A | 1/1990 | Dolphin et al. |
| 4,895,156 A | 1/1990 | Schulze |
| 4,914,720 A | 4/1990 | Knodle et al. |
| 4,919,891 A | 4/1990 | Yafuso et al. |
| 4,920,808 A | 5/1990 | Sommer |
| 4,954,318 A | 9/1990 | Yafuso et al. |
| 4,957,007 A | 9/1990 | Gray |
| 4,958,075 A | 9/1990 | Mace et al. |
| 4,968,632 A | 11/1990 | Brauer et al. |
| 4,973,718 A | 11/1990 | Buchler et al. |
| 4,989,456 A | 2/1991 | Stupecky |
| 5,012,809 A | 5/1991 | Shulze |
| 5,026,255 A | 6/1991 | Carpenter et al. |
| 5,030,420 A | 7/1991 | Bacon et al. |
| 5,034,189 A | 7/1991 | Cox et al. |
| 5,038,773 A | 8/1991 | Norlien et al. |
| 5,043,286 A | 8/1991 | Khalil et al. |
| 5,045,282 A | 9/1991 | Kritzman et al. |
| 5,047,350 A | 9/1991 | Switalski et al. |
| 5,061,076 A | 10/1991 | Hurley |
| 5,067,492 A | 11/1991 | Yelderman et al. |
| 5,081,041 A | 1/1992 | Yafuso et al. |
| 5,088,332 A | 2/1992 | Merilainen et al. |
| 5,092,342 A | 3/1992 | Hattendorff et al. |
| 5,094,959 A | 3/1992 | Allen et al. |
| 5,098,659 A | 3/1992 | Yim et al. |
| 5,111,827 A | 5/1992 | Rantala |
| 5,127,077 A | 6/1992 | Iyer et al. |
| 5,128,102 A | 7/1992 | Kaneko et al. |
| 5,137,026 A | 8/1992 | Waterson et al. |
| 5,152,287 A | 10/1992 | Kane |
| 5,153,436 A | 10/1992 | Apperson et al. |
| 5,173,432 A | 12/1992 | Lefkowitz et al. |
| 5,188,108 A | 2/1993 | Secker |
| 5,194,391 A | 3/1993 | Nauze et al. |
| 5,213,109 A | 5/1993 | Susi |
| 5,233,194 A | 8/1993 | Mauze et al. |
| 5,234,835 A | 8/1993 | Nestor et al. |
| 5,242,835 A | 9/1993 | Jensen |
| 5,244,810 A | 9/1993 | Gottlieb |
| 5,251,121 A | 10/1993 | Knodle et al. |
| 5,252,494 A | 10/1993 | Walt |
| 5,261,415 A | 11/1993 | Dussault |
| 5,262,192 A | 11/1993 | Nelson et al. |
| 5,285,783 A | 2/1994 | Secker |
| 5,285,784 A | 2/1994 | Seeker |
| 5,296,706 A | 3/1994 | Braig et al. |
| 5,308,581 A | 5/1994 | Lippitsch et al. |
| 5,308,771 A | 5/1994 | Zhou et al. |
| 5,326,585 A | 7/1994 | Nelson et al. |
| 5,344,810 A | 9/1994 | Hirata et al. |
| 5,347,843 A | 9/1994 | Orr et al. |
| 5,379,650 A | 1/1995 | Kofoed et al. |
| 5,398,695 A * | 3/1995 | Anderson et al. ........... 600/532 |
| 5,443,075 A | 8/1995 | Holscher |
| 5,445,160 A | 8/1995 | Culver et al. |
| 5,503,151 A | 4/1996 | Harnoncourt et al. |
| 5,511,547 A | 4/1996 | Markle et al. |
| 5,517,313 A | 5/1996 | Colvin, Jr. |
| 5,535,633 A | 7/1996 | Kofoed et al. |
| 5,570,697 A | 11/1996 | Walker et al. |
| 5,616,923 A | 4/1997 | Rich et al. |
| 5,625,189 A | 4/1997 | McCaul et al. |
| 5,670,097 A | 9/1997 | Duan et al. |
| 5,693,944 A | 12/1997 | Rich |
| 5,718,842 A | 2/1998 | Papkovsky et al. |
| 5,763,792 A | 6/1998 | Kullik |
| 5,789,660 A * | 8/1998 | Kofoed et al. .............. 600/532 |
| 5,804,048 A | 9/1998 | Wong et al. |
| 5,830,138 A | 11/1998 | Wilson |
| 5,836,300 A | 11/1998 | Mault |
| 5,863,460 A | 1/1999 | Slovacek et al. |
| 5,894,351 A | 4/1999 | Colvin, Jr. |
| 5,910,661 A | 6/1999 | Colvin, Jr. |
| 5,917,605 A | 6/1999 | Colvin, Jr. |

| | | | |
|---|---|---|---|
| 5,931,161 A | 8/1999 | Keilbach et al. | |
| 5,997,818 A | 12/1999 | Hacker et al. | |
| 6,015,715 A | 1/2000 | Kirschner et al. | |
| 6,044,843 A | 4/2000 | O'Neil et al. | |
| 6,095,986 A | 8/2000 | Braig et al. | |
| 6,102,868 A | 8/2000 | Banner et al. | |
| 6,190,327 B1 | 2/2001 | Isaacson et al. | |
| 6,203,502 B1 | 3/2001 | Hilgendorf et al. | |
| 6,309,360 B1 | 10/2001 | Mault | |
| 6,325,978 B1 * | 12/2001 | Labuda et al. | 600/532 |
| 6,402,698 B1 | 6/2002 | Mault | |
| 6,468,222 B1 | 10/2002 | Mault et al. | |
| 6,475,158 B1 * | 11/2002 | Orr et al. | 600/531 |
| 6,632,402 B2 * | 10/2003 | Blazewicz et al. | 422/84 |
| 6,815,211 B1 | 11/2004 | Blazewicz et al. | |

FOREIGN PATENT DOCUMENTS

| | | |
|---|---|---|
| FR | 2 538 550 | 6/1984 |
| GB | 699939 | 11/1953 |
| GB | 2032118 | 4/1980 |
| GB | 2052074 | 1/1981 |
| GB | 2 132 348 | 7/1984 |
| SU | 1509744 | 9/1989 |
| WO | WO 00/07498 | 2/2000 |
| WO | WO 00/13003 | 3/2000 |
| WO | WO 00/42418 | 7/2000 |
| WO | WO 00/70330 | 11/2000 |
| WO | WO 01/08554 A1 | 2/2001 |
| WO | WO 01/26547 A1 | 4/2001 |

OTHER PUBLICATIONS

"Basics of Auto Referencing," Sen. Sym., pp. 7-9 through 7-35, undated.
Blazewicz, Perry, et al., "A Novel Fast Oxygen Sensor with On-Airway, Breath-to-Breath Capability," vol. 15, Nos. 3-4, pp. 236-237, May 1999.
Burte, Edmund P., et al., "Microsystems for Measurement and Dosage of Volatile Anesthetics and Respirative Gases in Anesthetic Equipment," (undated).
"Capnostat II CO2 Sensor," $CO^2$ SMO User's Manual, p. 16, Apr. 27, 1993.
Datex Brochure, "See Compliance at a Glance," undated.
Flanagan, C.T., "A Novel Oxigraphy System Based on Oxygen Luminescence Quenching," Proceedings of the Rocky Mountain NASA Space Consortium, Apr. 1999.
Flanagan, C.T., "An Indirect Calorimetry System Based On a Novel Oxygen Luminescence Quenching Sensor," Ph.D. Dissertation Proposal presented to the Dept. of BioEngineering, Univ. of Utah, Sep. 22, 1999.
Flow Measurement, 1991, pp. 124, 125, 474, 475, 477, 500, 558.
Gewehr, P. M., Delpy, D. T.; "Optical oxygen sensor based on phosphorescence lifetime quenching and employing a polymer immobilised metalloporphyrin probe, Part 1 Theory and instrumentation;" pp. 1-10, Medical & Biological Engineering & Computing, Jan. 1993.
Gewehr, P. M., Delpy, D. T.; "Optical oxygen sensor based on phosphorescence lifetime quenching and employing a polymer immobilised metalloporphyrin probe, Part 2 Sensor membranes and results;" pp. 11-21, Medical & Biological Engineering & Computing, Jan. 1993.
Kolle, C., O'Leary, P.; "Optical Oxygen Sensor for Breath-Gas Analysis;" Report Institute for Chemical and Optical Sensors; Report No. COS 95.001, Feb. 1995.
Lutter, N., et al., "Calibration of an Infrared Multicomponent Analyzer for Mainstream Gas Monitoring," Anesthesiology, vol. 89, No. 3A, p. A945, Sep. 1998.
Lutter, N., et al., "Cross-Interferences of Volatile Anesthetic Agents on the Measurement of O2 Utilizing an Optical Fiber Sensor Based on Luminescence Quenching," 2000 ASA Meeting Abstracts, No. A-565, Oct. 17, 2000.
Miller, R.W., Flow Measurement Engineering Handbook, 1983, 9 pages.
Miller, R.W., Flow Measurement Engineering Handbook, 1989, 16 pages (unnumbered).
Moreno-Bondi, Maria C., et al., "New Luminescent Metal Complex for pH Transduction in Optical Fiber Sensing: Application to a CO2-Sensitive Device," Proc. SPIE, vol. 1368, pp. 157-164, Mar. 1991.
Neurauter, G., et al., "Fiber-Optic Microsensor for High Resolution pCO2 Sensing in Marine Environment," Fresenius J Anal Chem, 366(5), pp. 481-487, Mar. 2000.
Orr, et al., "A Respiratory Flowmeter Based on a Modified Mainstream $CO_2$ Cuvette," Abstract Presented at the Annual Meeting of the Society for Technology in Anesthesia, 3 pages (unnumbered, Feb. 17-19, New Orleans, LA.
Ower, E., et al., "The Characteristics of Pitot and Status Tubes in Incompressible Flow," The Measurement of Air Flow, 1966.
Rader, Con., "Pneumotachography," The Perkin Elmer Corporation, California Society of Cardiopulmonary Technologies Conference, Oct. 1982.
Saklad, Meyer, et al., "Pneumotachography: A New, Low-Dead Space, Humidity-Independent Device," Anesthesiology, vol. 5, No. 2, Aug. 1979, pp. 149-153.
SentrOxy, "A Rapid Optical Oxygen Sensor for the Lung Function Diagnostics," Sentronic GmbH, http://www.sentronic.de/company.
Sullivan, William J., et al., "Pneumotachography: Theory and Clinical Application," Respiratory Care, vol. 29, No. 7, Jul. 1984, pp. 736-749.
Voraberger, H.S., et al.; Novel oxygen optrode withstanding autoclavation: technical solutions and performance; pp. 1-7, Sensors and Actuator B 3679, 2000.
PCT International Search Report of Jul. 22, 2002.
Ammann, K., "What exactly is "permeation"?," Drager Review 82 (Oct. 1998), pp. 13-16.
EPA Article, "SITE Technology Capsule, ZENON Environmental, Inc., Cross-Flow Pervaporation System," EPN/540/R-95/511 a, Aug. 1995, 11 pages.
Journal of Clinical Monitoring and Computing, vol. 15, pp. 235-260 (1999).

* cited by examiner

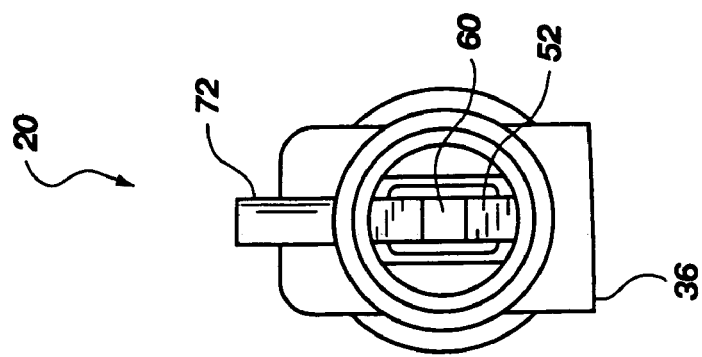
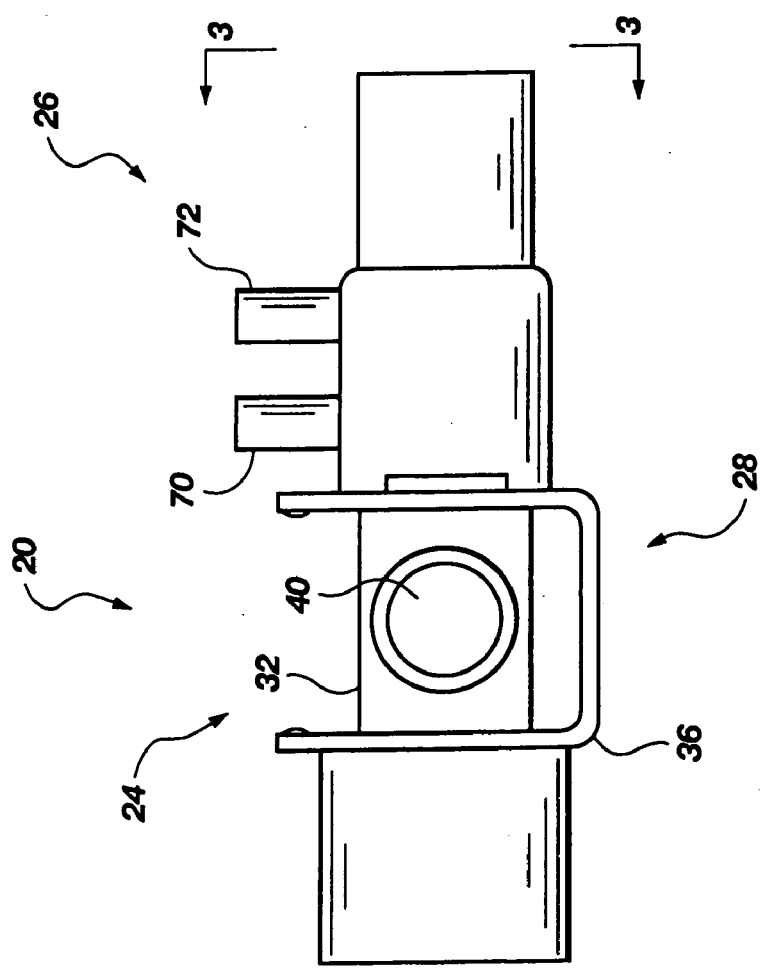
Fig. 3
Fig. 2

MULTIPLE FUNCTION AIRWAY ADAPTER

CROSS REFERENCE TO RELATED APPLICATIONS

This application is a continuation-in-part of application Ser. No. 09/092,260, filed Jun. 5, 1998, now U.S. Pat. No. 6,312,389, which is a continuation of application Ser. No. 08/680,492, filed Jul. 15, 1996, now U.S. Pat. No. 5,789,660. This application is also a continuation-in-part of applications Ser. No. 09/128,897, filed Aug. 4, 1998, now U.S. Pat. No. 6,815,211, and Ser. No. 09/128,918, filed Aug. 4, 1998, now U.S. Pat. No. 6,325,978.

BACKGROUND OF THE INVENTION

1. Field of the Invention

The present invention relates to an airway adapter which monitors the amounts of oxygen ($O_2$) in the respiration of an individual, as well as the respiratory flow of the amount of one or more of carbon dioxide ($CO_2$), nitrous oxide ($N_2O$), or an anesthetic agent other than nitrous oxide in the respiration of the individual. More specifically, the present invention relates to an integrated airway adapter which is capable of monitoring, by luminescence quenching techniques, the fractions, or concentrations, of gases such as $O_2$ in real time or breath-by-breath, as well as monitoring one or both of respiratory flow and, by infrared absorption techniques, the fractions, or concentrations, of gases such as $CO_2$, $N_2O$, and anesthetic agents.

2. Background of Related Art

Respiratory Gas Monitoring

Various types of sensors that are configured to communicate with the airway of a patient to monitor substances such as gases or vapors in the respiration of the patient are known in the art. Molecular oxygen, carbon dioxide and anesthetic agents, including nitrous oxide, are among the types of substances that may be detected with known sensors.

Typically, side-stream gas sensors are used during surgical procedures to indicate to an anesthesiologist the condition of a patient. Respiratory gas sensors may also be used in a variety of other medical procedures, such as heart stress tests with an individual on a treadmill, in other tests for monitoring the physical condition of an individual, and the like. Side-stream sampling requires the use of small bore sampling lines to draw gas from the breathing circuit for remote analysis. The problems associated with side-stream gas sampling are well known and include the following:

a) Impeding of the sample line by the presence of water and patient secretions;

b) Introduction of variable delay which creates synchronization difficulties when combining flow and gas concentration measures;

c) Loss of signal fidelity due to low pass filtering; and d) Handling of exhaust, which may contain anesthetic agents, blood, secretions, etc.

The use of mainstream sensors to monitor respiratory and anesthetic gases has the potential to solve the problems associated with side-stream sensors, especially when combining gas and flow and/or pressure signals.

Infrared Absorption

Infrared absorption has long been employed to detect and monitor gases, such as $CO_2$, $N_2O$, and other anesthetic agents, in the respiration of a patient. In infrared absorption techniques, infrared light of one or more wavelengths and of known intensity is directed into a stream of respiratory gases. The wavelength or wavelengths of such radiation are selected based on the gas or gases being analyzed, each of which absorbs one or more specific wavelengths of radiation. The intensity of the radiation which passes through the stream of respiratory gases, which radiation is typically referred to as "attenuated radiation", is measured and compared with the known intensity of the radiation emitted into the stream. This comparison of intensities provides information about the amount of amount of radiation of each wavelength that is absorbed by each analyzed gas, which, in turn, provides information about the amount (i.e., the concentration or fraction) of that gas in the patient's respiration.

U.S. Pat. Nos. 4,859,858 (hereinafter "the '858 Patent") and 4,859,859 (hereinafter "the '859 Patent"), both of which issued to Knodle et al. on Aug. 22, 1989, and U.S. Pat. No. 5,153,436 (hereinafter "the '436 Patent"), issued to Apperson et al. on Oct. 6, 1992, each disclose apparatus that include infrared absorption type sensors for measuring the amount of one or more specific gases in the respiration of a patient.

Typically, infrared gas sensors, such as those disclosed in the '858, '859, and '436 Patents, include a source from which infrared radiation is emitted. The emitted infrared radiation is focused into a beam by a mirror. The beam is transmitted through a sample of the gases being analyzed. After passing through the gases, the infrared radiation beam passes through a filter. The filter reflects all of the radiation except for the radiation in a narrow band which corresponds to a frequency absorbed by the gas of interest. This narrow band of radiation is transmitted to a detector, which produces an electrical output signal proportional in magnitude to the magnitude of the intensity of the infrared radiation impinging upon the detector. As the intensity of the radiation that passes through the filter is attenuated to an extent that is proportional to the concentration of a gas of interest, the strength of the signal generated by the detector is inversely proportional to the concentration of the gas of interest.

Infrared type gas sensors that are configured to substantially simultaneously measure the amounts of more than one type of gas in the respiration of a patient are also known. One such sensor, disclosed in U.S. Pat. No. 5,296,706 (hereinafter "the '706 Patent), issued to Braig et al. on Mar. 22, 1994, includes a plurality of discrete channels for facilitating the independent detection of six or more different anesthetic agents. The article, Burte, E. P., et al., "Microsystems for measurement and dosage of volatile anesthetics and respirative gases in anesthetic equipment," MEMS 98 Proceedings., The Eleventh Annual International Workshop on Micro Electro Mechanical Systems, pages 510-514 (1998) (hereinafter "the Burte Article"), discloses, among other things, a mainstream, multichannel sensor apparatus that is configured to simultaneously measure the amounts of a combination of anesthetic gases in the respiration of a patient.

Infrared type gas sensors typically employ a cuvette to sample the respiration of a patient via a nasal cannula or an endotracheal tube and a mechanical ventilator. The cuvette channels respiratory gases to a specific flow path and provides an optical path between an infrared radiation emitter and an infrared radiation detector, both of which can be detachably coupled to the cuvette.

A typical cuvette is molded from a polymer or other appropriate material and has a passage defining the flow path for the gases being monitored. The optical path crosses the flow path of the gases through windows in the sidewalls of the cuvette aligned along opposite sides of the flow passage allowing the beam of infrared radiation to pass through the cuvette.

The windows are generally formed from sapphire because of sapphire's favorable optical properties. However, sapphire is a relatively expensive material. Consequently, these cuvettes are almost invariably cleaned, sterilized, and reused. The cleaning and sterilization of a cuvette is time-consuming and inconvenient; and the reuse of a cuvette may pose a significant risk of contamination, especially if the cuvette was previously used in monitoring a patient suffering from a contagious and/or infectious disease.

Efforts have been made to reduce the cost of cuvettes by replacing the sapphire windows with windows fabricated from a variety of polymers. One of the major problems encountered in replacing sapphire cuvette windows with polymer windows is establishing and maintaining a precise optical path length through the sample being analyzed. This is attributable to such factors as a lack of dimensional stability in the polymeric material, the inability to eliminate wrinkles in the windows, and the lack of a system for retaining the windows at precise locations along the optical path.

Cuvette windows that are formed from polymers, including polypropylene, may limit the types of substances flowing through an airway adapter that may be monitored or measured by use of infrared techniques. This is because polymers typically include hydrocarbons, which may limit the transmissivity of polymers for some infrared and possibly other wavelengths of radiation that may be used to measure the amounts of certain substances.

U.S. Pat. No. 5,693,944 (hereinafter "the '944 Patent"), issued to Rich on Dec. 21, 1997, the disclosure of which is hereby incorporated in its entirety by this reference, discloses a cuvette, a method for using the same, and a method for manufacturing the same. The cuvette and methods of use disclosed in the '944 Patent eliminate the problems that were previously encountered in attempts to use polymers in the place of sapphire windows. The '944 Patent discloses fashioning windows from a malleable homopolymer, such as biaxially oriented polypropylene, in the thickness range of 0.001 to 0.005 inch. The use of this inexpensive polypropylene material allows for the fabrication of single-use, disposable cuvettes.

Luminescence Quenching

Luminescence quenching is a technique that has been used to measure oxygen concentrations in gases. In use of luminescence quenching to measure oxygen concentrations, a luminescable material is excited to luminescence. Upon exposure of the luminescing material to a gas mixture including oxygen, the luminescence is quenched, depending upon the amount (i.e., concentration or fraction) of oxygen to which the luminescable material is exposed, or the amount of oxygen in the gas mixture. Accordingly, the rate of decrease in the amount of luminescence, or quenching of luminescence, of the luminescable material (i.e., the amount of light emitted by the luminescable material) corresponds to the amount of oxygen in the gas mixture.

Typically, luminescence quenching requires the emission of excitation radiation from a source toward a luminescable material of a luminescence chemistry that may be quenched by, or is specific for, one or more types of gas (e.g., oxygen, carbon dioxide, halothane, etc.) to be measured. The excitation raditation causes the luminescable material to be excited and to emit electromagnetic radiation of a different wavelength than the excitation radiation. The presence of the one or more gases of interest quenches, or reduces the amount of radiation emitted from the luminescable material. The amount of radiation emitted from the luminescable material is measured by a detector and compared with the amount of radiation emitted from the luminescable material in the absence of one or more quenching gases in order to facilitate a determination of the amount of the one or more sensed, quenching gases in the respiration of a patient.

Luminescence quenching has been used in a variety of applications, including in diagnostic techniques. The use of luminescence quenching in mainstream oxygen sensors has also been disclosed. Nonetheless, these mainstream sensors are not equipped to employ other gas monitoring techniques or to measure respiratory flow, severely limiting the functionality of these luminescence quenching type sensors.

Respiratory Flow Monitoring

Respiratory flow measurement during the administration of anesthesia in intensive care environments and in monitoring the physical condition of athletes and other individuals prior to and during the course of training programs and medical tests provides valuable information for assessment of pulmonary function and breathing circuit integrity. Many different technologies have been applied to create a flow meter that meets the requirements of the critical care environment. Among the flow measurement approaches which have been used are:

1) Differential Pressure—measuring the pressure drop or differential across a resistance to flow;
2) Spinning Vane—counting the revolutions of a vane placed in the flow path;
3) Hot Wire Anemometer—measuring the cooling of a heated wire due to airflow passing around the wire;
4) Ultrasonic Doppler—measuring the frequency shift of an ultrasonic beam as it passes through the flowing gas;
5) Vortex Shedding—counting the number of vortices that are shed as the gas flows past a strut placed in the flow stream; and
6) Time of Flight—measuring the arrival time of an impulse of sound or heat created upstream to a sensor placed downstream.

Each of the foregoing approaches has various advantages and disadvantages, and an excellent discussion of most of these aforementioned devices may be found in W. J. Sullivan, G. M. Peters, P. L. Enright, M.D, "Pneumotachographs: Theory and Clinical Application," Respiratory Care, July 1984, Vol. 29-7, pp. 736-49, and in C. Rader, Pneumotachography, a report for the Perkin-Elmer Corporation presented at the California Society of Cardiopulmonary Technologists Conference, October 1982.

At the present time, the most commonly used device for respiratory flow detection is the differential pressure flow meter. The relationship between flow and the pressure drop across a restriction or other resistance to flow is dependent upon the design of the resistance. Many different resistance configurations have been proposed. The goal of many of these configurations is to achieve a linear relationship between flow and pressure differential.

In some differential pressure flow meters, which are commonly termed "pneumotachs", the flow restriction has been designed to create a linear relationship between flow and differential pressure. Such designs include the Fleisch pneumotach in which the restriction is comprised of many small tubes or a fine screen to ensure laminar flow and a linear response to flow. Another physical configuration is a flow restriction having an orifice that varies in relation to the flow. This arrangement has the effect of creating a high resistance at low flows and a low resistance at high flows. Among other disadvantages, the Fleisch pneumotach is susceptible to performance impairment from moisture and mucous, and the variable orifice flow meter is subject to material fatigue and manufacturing variabilities.

Most all known prior art differential pressure flow sensors suffer deficiencies when exposed to less than ideal gas flow inlet conditions and, further, possess inherent design problems with respect to their ability to sense differential pressure in a meaningful, accurate, repeatable manner over a substantial dynamic flow range. This is particularly true when the flow sensor is needed to reliably and accurately measure low flow rates, such as the respiratory flow rates of infants.

U.S. Pat. No. 5,379,650 (hereinafter "the '650 Patent"), issued to Kofoed et al. on Jan. 10, 1995, the disclosure of which is hereby incorporated in its entirety herein by this reference, has overcome the vast majority of the problems with differential pressure flow sensors with a sensor that includes a tubular housing containing a diametrically-oriented, longitudinally extending strut. The strut of the flow sensor disclosed in the '650 Patent includes first and second lumens with longitudinally-spaced pressure ports that open into respective axially-located notches formed at each end of the strut.

Developments in patient monitoring over the past several decades have shown that concurrent measurements of various combinations of exhaled gas flow rate, $O_2$ concentrations, $CO_2$ concentrations, and concentrations of $N_2O$ and various other anesthetic agents provide information that is useful in decision-making with respect to anesthesia and therapy. By combining flow, airway pressure, $CO_2$, and $O_2$ measurements, one can calculate $CO_2$ elimination ($VCO_2$) and $O_2$ consumption ($VO_2$), which are related to the metabolic status of an individual. Also, these measurements can provide a graphical representation of the expired $O_2$ or $CO_2$ concentration versus expired volume which provides information about gas exchange in different compartments of the lungs.

While integrated adapters that include both flow and infrared $CO_2$ sensors are known, separate apparatus are presently necessary to obtain $O_2$ measurements and measurements of respiratory flow or of $CO_2$ or $N_2O$ and other anesthetic agents. The various apparatus that are needed to simultaneously acquire a combination of the respiratory $O_2$ signals, respiratory flow signals, airway pressure signals, and signals representative of amounts of $CO_2$, $N_2O$, or anesthetic agents would require multiple components, if such components were all available in a mainstream configuration. Such "stacking" of multiple sensors at the patient's airway is cumbersome and adds undesirable volume (dead space) and resistance to the breathing circuit.

It would be highly desirable to have an airway adapter which combines a luminescence quenching sensor with one or both of an infrared gas sensor and a respiratory flow sensor in a configuration which is convenient to use and which minimizes phase lag and internal dead space of the combination.

SUMMARY OF THE INVENTION

The present invention includes an integrated airway adapter for monitoring, in real time, breath-by-breath amounts of substances, such as $O_2$, $CO_2$, $N_2O$, and anesthetic agents in the respiration of an individual, which includes normal respiratory gases, as well as other substances that are inhaled and exhaled by the individual. The airway adapter of the present invention is a compact adapter that integrates at least two functions into a single unit that meets the requirements for clinical patient monitoring. The airway adapter may include a combination of different types of substance detection components or a combination of one or more substance detection components and a respiratory flow detection component.

An $O_2$ sensing portion of an integrated airway adapter incorporating teachings of the present invention may include a quantity of luminescence quenching material located in communication with a flow path along which respiratory gases are conveyed through the airway adapter so as to be exposed to the respiratory gases. The luminescable material of the $O_2$ sensing portion may be carried by a removable, replaceable portion of the airway adapter to facilitate reuse of the airway adapter. A source of excitation radiation may be configured to be coupled to the airway adapter so as to direct radiation through a window of the airway adapter and toward the luminescable material to excite the same to luminesce, or to emit radiation. The amount of radiation emitted from the excited luminescable material may be measured with a detector, which may also be configured for assembly with the airway adapter, which detects emitted radiation through a window of the airway adapter.

The integrated airway adapter may also include a flow sensor. Preferably, the flow sensor is a pneumotach that includes two pressure ports, which facilitate the generation of a differential pressure across an orifice of the pneumotach. One of the pressure ports may facilitate monitoring of airway pressure. Alternatively, the flow sensor may have more than two ports, with at least one of the ports facilitating measurement of the airway pressure. The respiratory flow sensor preferably has the capability of accommodating a wide variety of gas flow inlet conditions without adding significant system volume or excessive resistance to the flow of respiration through the integrated airway adapter of the present invention. The design of the respiratory flow sensor of the present invention may also substantially inhibit the introduction of liquids into the pressure ports or monitoring system of the sensor.

The flow sensor may include a flow resistance element (whether the strut or the gas concentration monitoring portion) which creates a nonlinear differential pressure signal. To obtain adequate precision at extremely high and low flow rates, a very high resolution (e.g., 18-bit or 20-bit) analog-to-digital (A/D) conversion device may be used. The use of such a very high resolution A/D converter allows a digital processor to compute flow from the measured differential pressure by using a sensor characterizing look-up table. This technique eliminates the need for variable or multiple gain amplifiers and variable offset circuits that might otherwise be required with use of a lower resolution A/D converter (e.g., a 12-bit A/D converter).

Alternatively, or in addition to the flow sensor, an integrated airway adapter incorporating teachings of the present invention may include gas sensor configured to measure amounts of $CO_2$, $N_2O$, or anesthetic agents in the respiration of an individual. As an example, the airway adapter may include a gas sensor that employs infrared absorption techniques. Such an exemplary gas sensor may include a chamber with a pair of opposed, substantially axially aligned windows flanking a flow path through the airway adapter. The windows preferably have a high transmittance for radiation in at least the intermediate infrared portion of the electromagnetic spectrum. It is essential to the accuracy of the infrared gas sensor that the material used for the windows transmit a usable part of the infrared radiation impinging upon thereupon. Thus, the window material must have appropriate optical properties. Preferred window materials include, but are not limited to, sapphire and biaxially oriented polypropylene. Substantial axial alignment of the windows allows an infrared radiation beam to travel from a source of infrared radiation, transversely through the chamber and the gas(es) flowing through the chamber, to an infrared radiation detector. Alternatively, the airway adapter may include a single window and a reflective element, such as a mirror or reflective coating. These elements facilitate the direction of infrared radiation into and across the chamber and the reflection of the infrared radiation back across and out of the chamber to a radiation detector. Signals from the detector facilitate determination of the amounts (i.e., concentrations or fractions) of one or more gases, such as $CO_2$, $N_2O$, and anesthetic agents, in respiration flowing through the chamber.

The integrated airway adapter can be either reusable or disposable. If the airway adapter is designed to be disposable, the infrared absorption windows and the windows that facilitate detection of luminescence quenching should be made of an inexpensive material. If the airway adapter is designed to be reused, the windows of the infrared gas sensor may be detachable from the remainder of the airway adapter so as to facilitate the cleaning and sterilization of nondisposable windows. Alternatively, the windows may remain on the airway adapter during cleaning and sterilization thereof. If luminescable material is carried upon any portion of one or both windows, the luminescable material may be removed from the windows during cleaning and subsequently replaced or, if the luminescable material will withstand the cleaning a sterilization processes, the luminescable material may remain on the windows during these processes.

Injection molding processes may be used to manufacture the airway adapter of the present invention. The consistency of product obtainable from the injection molding process provides a high degree of interchangeability, thereby eliminating the need for a calibration procedure to be performed during setup or with disposable adapter replacement.

In addition, the integrated airway adapter may incorporate a specific instrument connection scheme to facilitate the proper assembly of external components (e.g., an infrared emitter and detector, a luminescence quenching source and detector, etc.) with the airway adapter, as well as to facilitate the proper assembly of the airway adapter with a respiratory airway. For example, but not to limit the scope of the present invention, the airway adapter may include colors, optical coding, or other suitable types of coding to facilitate correct assembly or may be configured so as to prevent improper assembly.

Other features and advantages of the present invention will become apparent to those of ordinary skill in the art through a consideration of the ensuing description, the accompanying drawings, and the appended claims.

BRIEF DESCRIPTION OF THE DRAWINGS

FIG. 2 is a side elevation view of a first preferred embodiment of the airway adapter of the present invention;

FIG. 3 is an end elevation view of the airway adapter of FIG. 2, looking from plane 3-3;

DETAILED DESCRIPTION OF THE PREFERRED EMBODIMENTS

Figure 1:
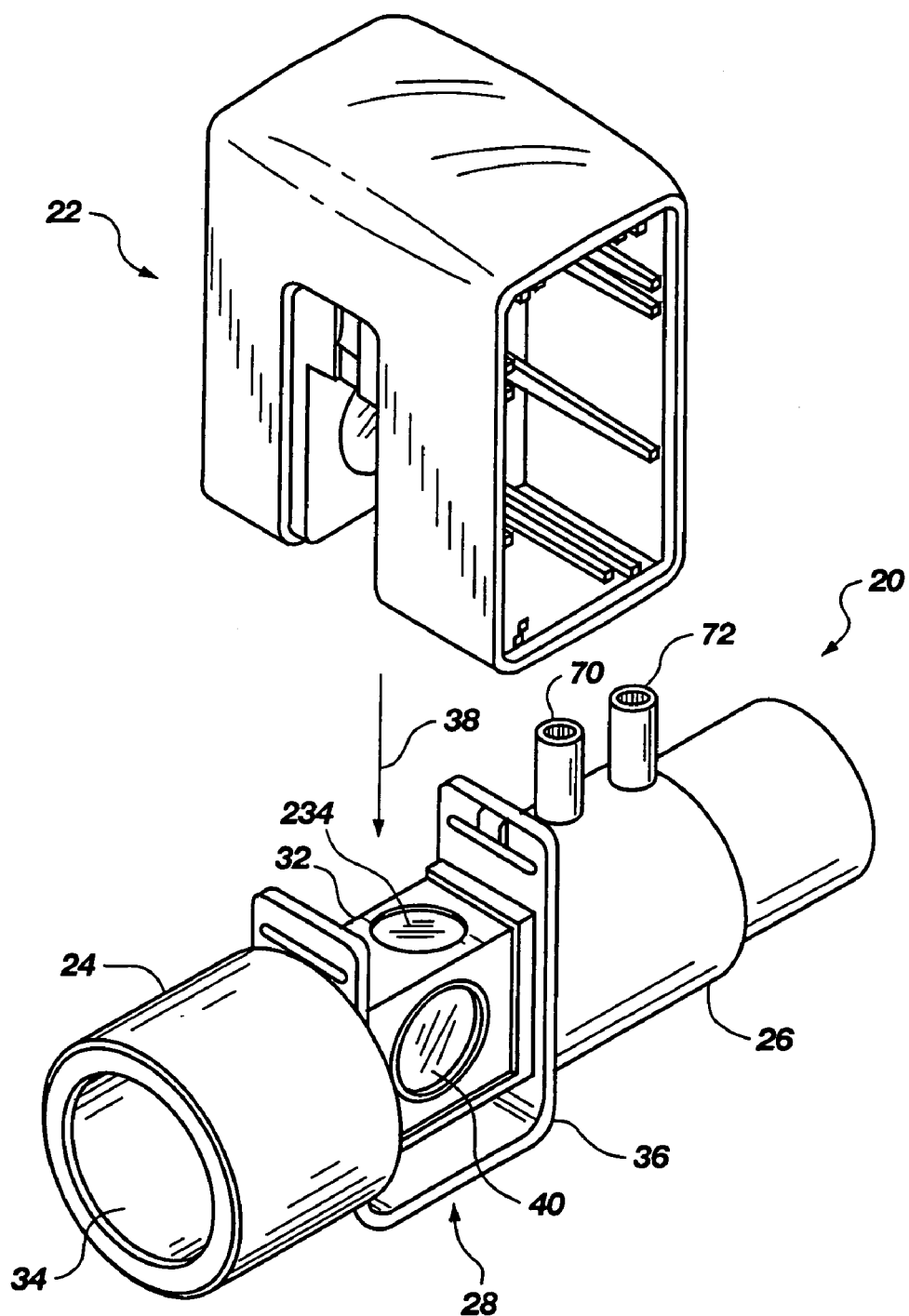
FIG. 1 is an exploded perspective view of a first preferred embodiment of the airway adapter of the present invention in combination with a transducer housing for containing electronics for respiratory and anesthetic agent gas determination.

FIGS. 1-5 illustrate an exemplary airway adapter 20 embodying teachings of the present invention. Airway adapter 20 is preferably a unitary, injection-molded plastic element, so as to afford low manufacturing cost and permit disposal of the sensor after a single use, with a separate transducer housing 22 containing an infrared emitter 252, an infrared detector 254, a luminescence excitation radiation source 256, and a luminescence detector 258 (FIG. 6). However, this configuration is not a requirement. As illustrated, airway adapter 20 has a generally parallelepipedal center section 32 between and axially aligned with first and second tubular portions 24 and 26, with a flow passage 34 extending from end-to-end through airway adapter 20.

The illustrated airway adapter 20 is designed for connection with a breathing circuit that communicates with the airway of a patient. Airway adapter 20 may be connected between a patient ventilation device and the tubing of a mechanical ventilator. For example, first tubular portion 24 of airway adapter 20 may be connected to an endotracheal tube inserted in the trachea of a patient, while second tubular portion 26 of airway adapter 20 is attached to the tubing of the mechanical ventilator. Alternatively, airway adapter 20 may be connected to a breathing mask or other apparatus that are less invasive than endotracheal tubes. Airway adapter 20 need not be connected to a mechanical ventilator, but may be connected with a source of respiratory gases (e.g., an oxygen source) or communicate directly with the air from the patient's environment. As shown, first and second tubular portions 24 and 26 have bores of varying diameter and substantially circular cross-sections, with a gas concentration monitoring portion 28 disposed therebetween. Second tubular portion 26 houses a respiratory flow monitoring device 30.

Figure 4:
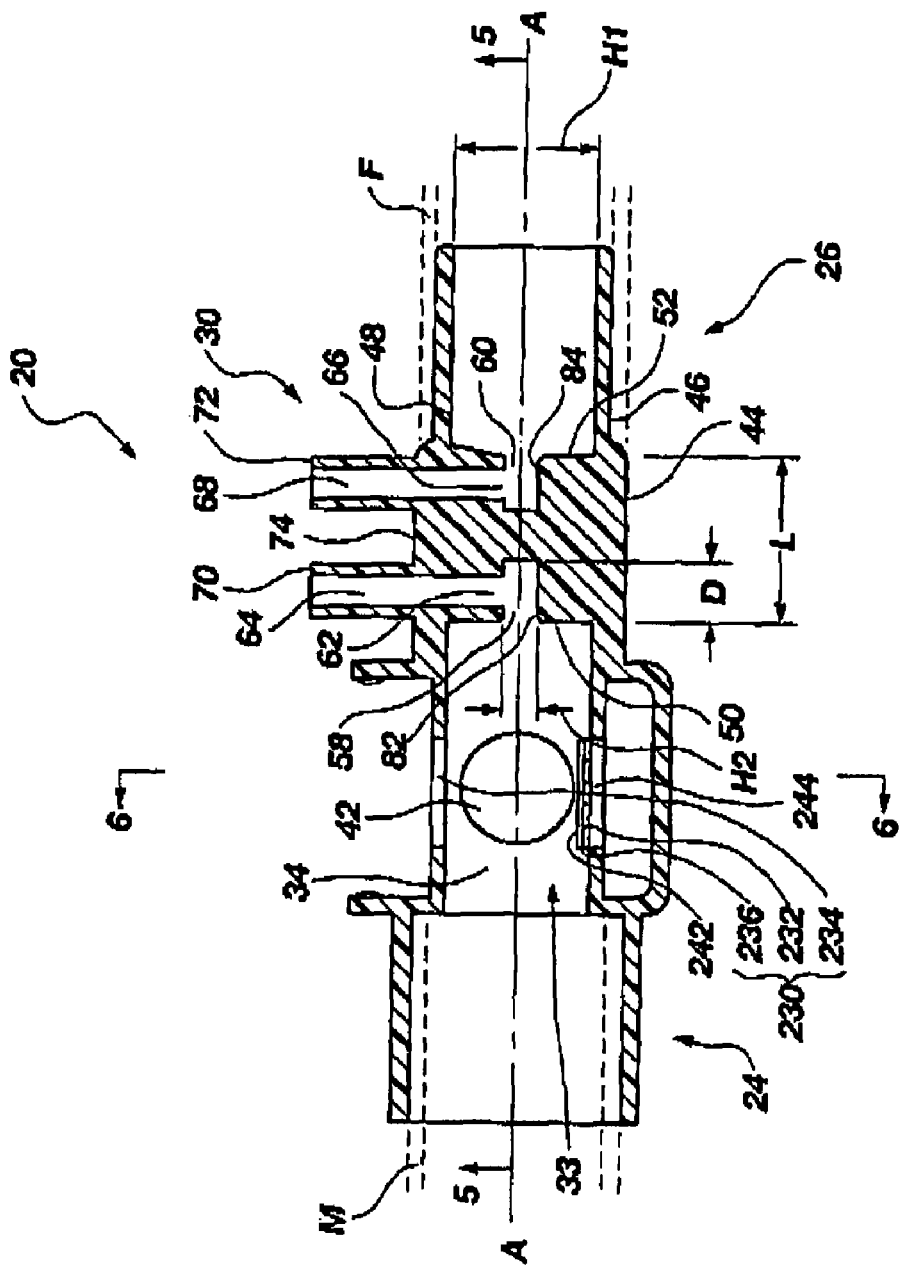
FIG. 4 is a side sectional elevation view of the airway adapter of FIG. 2.
Figure 2A:
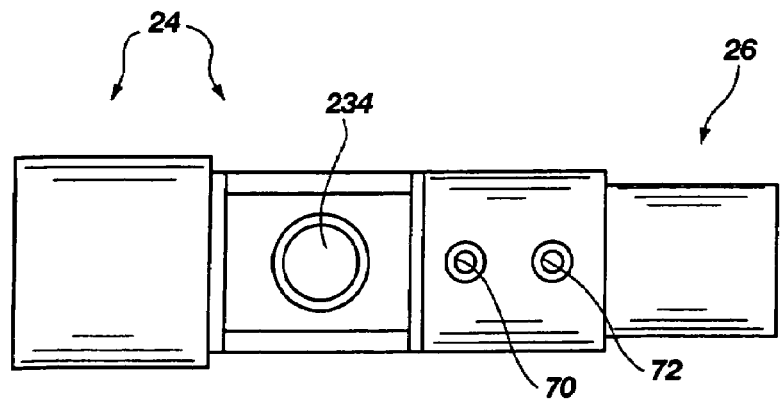
FIG. 2A is top elevation view of a first preferred embodiment of the airway adapter of the present invention.

Gas concentration monitoring portion 28 includes a gas sensing portion 230, which is configured to employ luminescence quenching techniques to measure the partial pressure or amount of oxygen or other gases that flow through airway adapter 20. As illustrated in FIGS. 1, 2A, 4 and 5, gas sensing portion 230, also referred to as "gas sensor 230," includes a quantity of luminescable material 232 exposed to a flow passage 34 that extends through airway adapter 20. Gas sensing portion 230 also includes a window 234 for facilitating the excitation of luminescable material 232 or some combination of luminescable materials with radiation of one or more excitation wavelengths, as well as the measurement of the intensities of one or more wavelengths of radiation that are emitted from luminescable material 232, as illustrated in FIGS. 1, 2A, and 4. Window 234 preferably has a high transmittance for wavelengths of excitation radiation, which excites luminescable material 232, and for wavelengths of radiation emitted from luminescable material 232.

Figure 5:
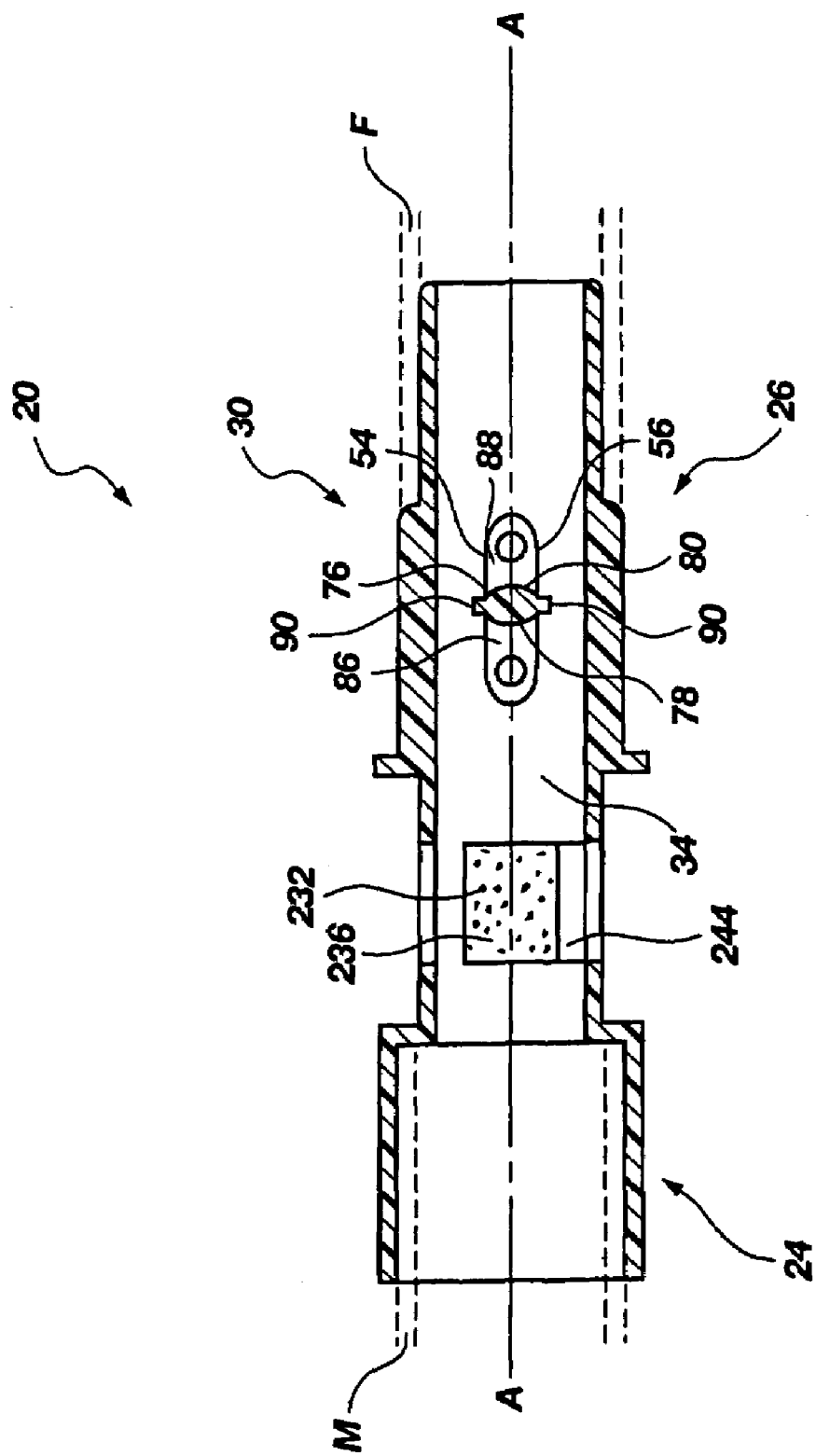
FIG. 5 is a sectional view of the airway adapter of FIG. 4, looking upward from plane 5-5 extending laterally across the axis of the present invention.
Figure 6:
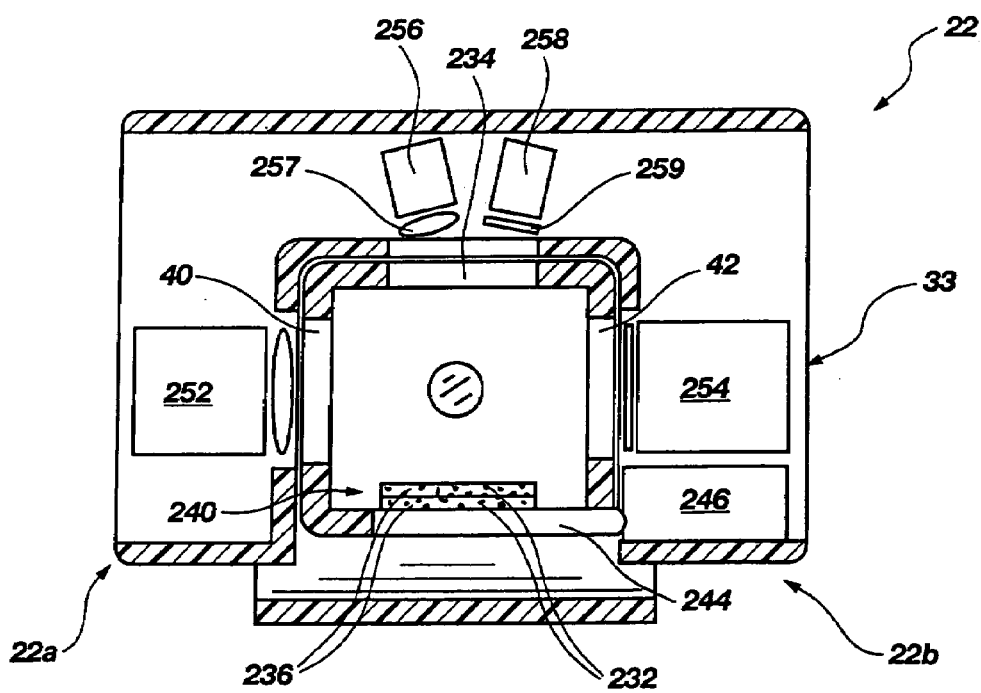
FIG. 6 is another sectional elevation view of the airway adapter of FIGS. 2 and 4, looking from plane 6-6 of FIG. 4, and schematically illustrating a transducer assembled therewith.

With specific reference to FIGS. 4 and 5, luminescable material 232 is preferably carried by a membrane 236, or matrix, which is disposed on or comprises an integral part of a surface of flow passage 34. Alternatively, a membrane 236 carrying luminescable material 232 may be located in another portion of airway adapter 20 that communicates with flow passage 34.

Luminescable material 232 may be dispersed throughout passages or openings formed in membrane 236. The passages and openings through membrane 236 may have diameters or widths of about 0.1 μm to about 10 μm, as the diffusion constant for molecular oxygen through membranes of such dimensions is large enough to provide a luminescence quenching response time of sufficiently short duration to facilitate a measurement of luminescence quenching rate on a breath-by-breath basis, or in real time. Stated another way, these membrane 236 dimensions facilitate the substantially immediate exposure of luminescable material 232 to oxygen and other luminescence quenching substances as these substances flow through or past membrane 236.

If airway adapter 20 is reusable, membrane 236 may be removable from the remainder of airway adapter 20 so as to facilitate replacement thereof with a new membrane 236 carrying luminescable material 232 and, thus, to facilitate accurate determinations of the concentration of oxygen or other gases with subsequent use of airway adapter 20. Alternatively, if luminescable material 232 will withstand the cleaning and sterilization processes to which airway adapter 20 is subjected, membrane 236 may be permanently secured to airway adapter 20 and reused following cleaning and sterilization thereof.

Porphyrins are an example of a material that may be used as luminescable material 232. Porphyrins are stable organic ring structures that often include a metal atom. When the metal atom is platinum or palladium, the phosphorescence decay time ranges from about 10 μs to about 1,000 μs. Porphyrins are also sensitive to molecular oxygen. When porphyrins are used as luminescable material 232, it is preferred that the porphyrins retain substantially all of their photo-excitability with repeated use. Stated another way, it is preferred that the porphyrins be "photostable." Fluorescent porphyrins, such as meso-tetraphenyl porphines, are particularly photostable. The various types of porphyrins that may be used as luminescable material 232 to facilitate oxygen detection include, without limitation, platinum meso-tetra(pentafluoro)phenyl porphine, platinum meso-tetraphenyl porphine, palladium meso-tetra(pentafluoro)phenyl porphine, and palladium meso-tetraphenyl porphine. Of course, other types of luminescable materials that are known to be quenched upon being exposed to oxygen, carbon dioxide, or another analyzed substance (e.g., gas, liquid, or vapor) may also be used in airway adapters incorporating teachings of the present invention.

Membrane 236 is preferably formed from a material that is compatible with luminescable material 232. Moreover, it is preferred that the material of membrane 236 be compatible with respiratory gases, as well as non-toxic to the patient and, preferably, to the environment.

Materials that may be used to form membrane 236 include, but are not limited to, porous polyvinylchloride (PVC), polypropylene, polycarbonate, polyester, polystyrene, polymethacrylate polymers, and acrylic copolymers. Specifically, microporous polycarbonate filtration membranes available from Pall Gelman Sciences of Ann Arbor, Mich., and from Whatman, Inc. of Clifton, N.J., (track-etched microporous polycarbonate filtration membranes with a thickness of about 10 μm and a pore size of about 0.4 μm) are useful as membrane 236.

As indicated previously herein, it is preferred that membrane 236 be permeable to respiratory gases, including oxygen. As respiratory gases flow past, into, or through membrane 236, the respiratory gases, including oxygen, contact luminescable material 232 carried thereby. The luminescence of, or intensity of radiation emitted from, luminescable material 232 is then quenched to a degree that is based on the amount of oxygen or other luminescence quenching gases in the respiratory gases. The permeability of membrane 236 to respiratory gases also has an affect on the number of luminescable material 232 particles that is exposed to the respiratory gases and may, therefore, affect the amount of luminescence quenching that occurs as luminescable material 232 is exposed to oxygen and other luminescence quenching gases present in the respiratory gases that flow through membrane 236.

Luminescable material 232 may be applied to membrane 236 by known processes. By way of example and not to limit the scope of the present invention, a solvent may be used to introduce luminescable material 232 onto a surface of membrane 236, as well as into openings thereof. Preferably, the solvent does not substantially dissolve the material of membrane 236. The solvent may, however, interact with the material of membrane 236 in a manner that causes membrane 236 and the openings thereof to swell, so as to facilitate the introduction of luminescable material 232 into the openings. Exemplary solvents that may be used to apply luminescable material 232 to membrane 236 include, without limitation, hexane, petroleum ethane, toluene, tetrahydrofuran, methylene chloride, trichloroethylene, xylene, dioxane, isopropyl alcohol, and butanol, as well as mixtures of any of the foregoing. Of course, the use of a particular solvent depends on its compatibility with both luminescable material 232 and with the material of membrane 236. Once luminescable material 232 has been applied to membrane 236, the solvent may be evaporated or otherwise removed from membrane 236 in a manner that leaves luminescable material 232 on the surface and within the openings of membrane 236.

Alternatively, as shown in FIG. 6, luminescable material 232 may be sandwiched between two membranes 236. A solvent that will not significantly degrade luminescable material 232 dissolves the material of membranes 236 enough to bond membranes 236 to one another to form a single composite membrane 240, but without substantially altering the structures of membranes 236. Luminescable material 232 remains between membranes 236 and may at least partially permeate membranes 236. As membranes 236 trap luminescable material 232 therebetween, increased concentrations of luminescable material 232 may be incorporated into composite membrane 240 relative to the concentration of luminescable material 232 contained by a single membrane 236.

With returned reference to FIG. 4, sensor 230 may include an overcoat layer 242 over membrane 236. Overcoat layer 242 may be formed from a polymer, such as the same type of polymer from which membrane 236 is formed, or from a different type of polymer than that from which membrane 236 is formed. Overcoat layer 242 does not substantially prevent gases in the respiration of an individual from contacting luminescable material 232. Overcoat layer 242 may also refine or tailor various properties of membrane 236, including, without limitation, the light absorption properties of membrane 236, the light transmission properties of membrane 236, and the permeability of membrane 236 to various gases. As an example of the use of an overcoat layer 242 to tailor the properties of membrane 236, permeability of membrane 236 to oxygen or other respiratory gases may be reduced by applying to membrane 236 an overcoat layer 242 formed from a less permeable material.

Known processes may be used to apply overcoat layer 242 to membrane 236. For example, a dissolved polymer may be applied to membrane 236 to form overcoat layer 242. Alternatively, a preformed overcoat layer 242 may be adhered to membrane 236 by known means, so long as the overcoated membrane 236 retains the desired properties.

In use of gas sensor 230, membrane 236 thereof is preferably disposed over a thermal source of a known type, such as thermal capacitor 244. Thermal capacitor 244 communicates with a heater component 246 (FIG. 6), which heats thermal capacitor 244 to a desired, substantially constant temperature. Because thermal capacitor 244 contacts membrane 236, thermal capacitor 244, in turn heats membrane 236 to a substantially constant temperature. Accordingly, thermal capacitor 244 substantially prevents temperature changes of member 236 or of luminescable material 232 thereon from affecting the luminescence quenching caused by oxygen or other substances flowing past luminescable material 232.

One example of the manner in which thermal capacitor 244 and heater component 246 may communicate with each other includes providing a floating, thermally conductive heater component 246 on transducer housing 22 (FIGS. 6). Upon coupling transducer housing 22 with airway adapter 20, heater component 246 and thermal capacitor 244 contact one another in such a manner as to provide an efficient transfer of heat from heater component 246 to thermal capacitor 244.

Transducer housing 22, as depicted in FIG. 6, at least partially contains a radiation source 256, which emits electromagnetic excitation radiation of one or more wavelengths that will excite luminescable material 232 into luminescence. For example, radiation source 256 may comprise a light-emitting diode (LED), which produces excitation radiation in the form of visible light. Radiation source 256 preferably emits excitation radiation of wavelengths that will excite luminescable material 232 to emit a desired intensity of radiation. Excitation radiation emitted from radiation source 256 passes through and is focused by a lens 257, which directs the focused excitation radiation toward luminescable material 232.

Transducer housing 22 also contains at least a portion of a detector 258 positioned to receive radiation emitted from luminescable material 232 and configured to measure an intensity of such emitted radiation. Accordingly, detector 258 is positioned toward window 234 and toward luminescable material 232. Preferably, a filter 259 is disposed between luminescable material 232 and detector 258 so as to prevent wavelengths of electromagnetic radiation other than those emitted from luminescable material 232 from interfering with the luminescence and luminescence-quenching measurements obtained with detector 258. Other features and advantages of a luminescence quenching type sensor that may also be employed in the present invention are disclosed in U.S. Pat. Nos. 6,815,211 and 6,325,978, filed on Aug. 4, 1998, both of which have been assigned to the same assignee as the present invention, the disclosures of which are hereby incorporated in their entireties by this reference.

Gas concentration monitoring portion 28 of airway adapter 20 provides a seat for transducer housing 22. An integral, U-shaped casing element 36 positively locates transducer housing 22 across airway adapter 20 and in the transverse direction indicated by arrow 38 in FIG. 1. Arrow 38 also shows the direction in which transducer housing 22 is displaced to detachably assemble it to airway adapter 20. In a preferred embodiment, transducer housing 22 snaps into place on airway adapter 20, as disclosed in the '858 and '859

Patents; no tools are needed to assemble adapter 20 and transducer housing 22 or to remove transducer housing 22 from airway adapter 20.

Center section 32 may also include an infrared sensor portion 33 with first and second axially aligned windows 40 and 42, respectively (only window 42 is shown in FIG. 4). Windows 40 and 42 preferably have a high transmittance for radiation in at least the intermediate infrared portion of the electromagnetic spectrum. The substantial axial alignment of first window 40 and second window 42 allows an infrared radiation beam to travel from infrared radiation emitter 252 in one leg 22a of transducer housing 22, transversely through airway adapter 20 and the one or more gases flowing through flow passage 34 of airway adapter 20, to infrared detector 254 in the opposing, substantially parallel leg 22b of transducer housing 22.

Cuvette windows 40 and 42 for infrared absorption measurements have typically been fabricated from sapphire because of sapphire's favorable optical properties, stability, and resistance to breakage, scratching, and other forms of damage. Alternatively, the cost of the cuvette can be reduced to the point of making it practical to dispose of the cuvette after a single use by fabricating the cuvette windows from an appropriate polymer. It is essential to the accuracy of infrared absorption portion of the gas concentration monitor that the polymer transmit a usable part of the infrared radiation impinging upon it. Thus, the window material must have the appropriate optical properties for measuring the desired substances. An exemplary window material exhibiting such properties with respect to measuring an amount of carbon dioxide present in the respiration of a patient is biaxially oriented polypropylene. Other materials may also be used, depending upon the transmissivities thereof for certain wavelengths of radiation that are to be used to detect the presence or amounts of particular substances in the respiration of a patient.

Referring again to FIGS. 1 and 6, a transducer housing 22 is illustrated which carries electronic components that are designed to facilitate the output of one or more reference signals and one or more signals related to the concentrations of corresponding respiratory or anesthetic gases flowing through airway adapter 20. An infrared radiation emitter 252 of transducer housing 22 is configured to direct infrared radiation of one or more wavelengths into center section 32 of airway adapter 20 through window 40, through a sample of respiratory gases within center section 32, and out of center section 32 through window 42. Infrared detector 254, which is positioned adjacent window 42 when transducer housing 22 is assembled with airway adapter 20, is positioned to receive infrared radiation signals that exit center section 32 of airway adapter 20 through window 42.

The internal configuration and design of infrared detector 254, which preferably monitors, in real time, the amounts of $CO_2$, $N_2O$, or anesthetic agents in the respiration of an individual is thoroughly discussed in U.S. Pat. No. 5,616,923 (hereinafter "the '923 Patent"), incorporated herein in its entirety by this reference. It is understood that infrared $CO_2$ monitor devices such as those disclosed in the '858, '859, and '436 Patents, as well as other $CO_2$ detection devices, could be used in transducer housing 22. In addition to one or more infrared sensors, infrared detector 254 may include any combination of other components, including a reference sensor, optics (e.g., lenses, filters, mirrors, beam splitters, etc.), coolers, and the like.

The infrared signals detected by infrared detector 254 can be ratioed to provide a signal accurately and dynamically representing the amount of $CO_2$, $N_2O$, or an anesthetic agent flowing through airway adapter 20.

Figure 7:
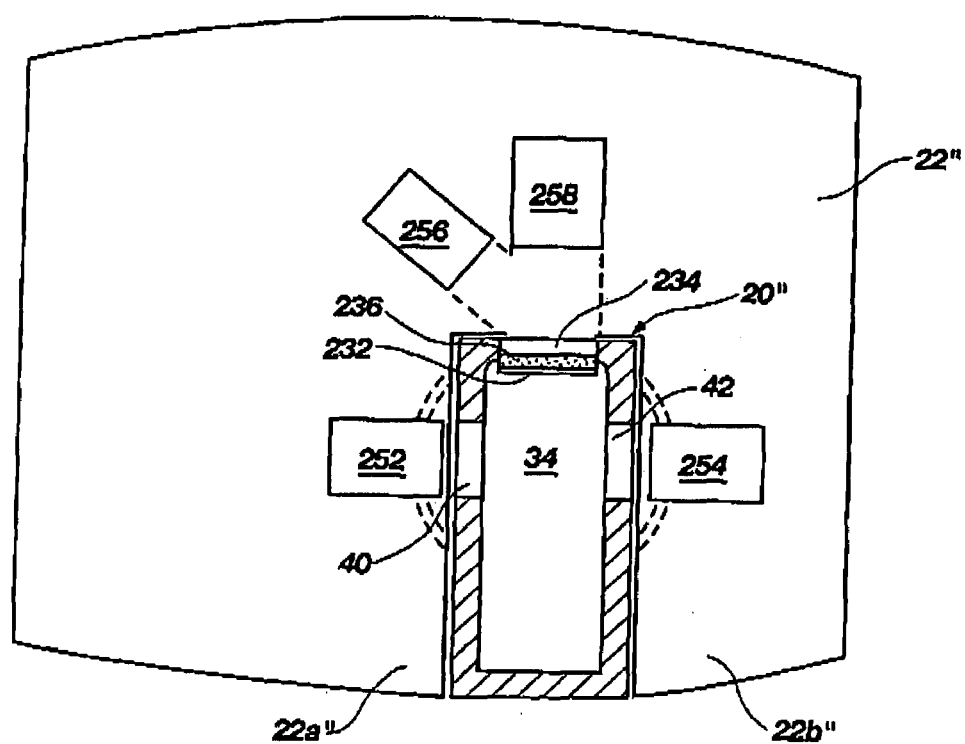
FIG. 7 is a cross-sectional representation of an airway adapter that includes a single window through which a luminescence quenching measurement of one or more substances may be obtained and a pair of opposed windows through which an infrared measurement of one or more substances may be obtained.

FIG. 7 illustrates another embodiment of airway adapter 20" and of a complementary transducer housing 22" assembled therewith.

Airway adapter 20" includes a window 234 formed through a top portion thereof. Window 234 is transparent to (i.e., has a high transmissivity for) wavelengths of radiation that are used to excite luminescable material 232 on a membrane 236 positioned within flow passage 34 and adjacent to window 234. In addition, window 234 is transparent to one or more wavelengths of radiation that are emitted from luminescable material 232 and quenched by an analyzed substance to a degree that relates to an amount of the analyzed substance in respiration of an individual or in another gas mixture.

In addition, airway adapter 20" includes windows 40, 42 positioned on opposite sides of flow passage 34. Windows 40 and 42 facilitate the direction of radiation of one or more specified infrared wavelengths across flow passage 34 to facilitate the measurement of amounts of one or more substances, such as carbon dioxide or nitrous oxide or other anesthetic agents, that are present in the respiration of an individual as the individual's respiration passes through a location of flow passage 34 between which windows 40 and 42 are positioned. Accordingly, windows 40 and 42 are each preferably formed from a material that is substantially transparent to (i.e., has a high transmissivity for) infrared wavelengths that are desired for use in measuring amounts of one or more substances in respiration of the individual.

Transducer housing 22" contains at least a portion of a radiation source 256 positioned to direct one or more wavelengths of radiation that are capable of exciting luminescable material 232 into luminescence through window 234, toward luminescable material 232. Radiation source 256 may include optics (e.g., filters, lenses, beam splitters, etc.) that direct radiation toward the appropriate location and that filter out one or more undesirable wavelengths of the radiation emitted from radiation source 256. In addition, transducer housing 22" carries a luminescence detector 258, as well as any optics (e.g., filters, lenses, beam splitters, etc.) associated therewith, which are respectively positioned to receive and detect at least one wavelength or radiation that is emitted by luminescable material 232 and that is quenched by exposure to a substance of interest to a degree that indicates an amount of the substance to which luminescable material 232 is exposed.

An infrared emitter 252 and an infrared detection component 254 are positioned in opposite legs 22a", 22b", respectively, of transducer housing 22". Infrared emitter 252 is oriented within transducer housing 22" so as to direct one or more infrared wavelengths of radiation through window 40, across flow passage 34, and through window 42 as transducer housing 22" is assembled with airway adapter 20". Infrared detection component 254, which is positioned adjacent window 42 when transducer housing 22" is assembled with airway adapter 20", is oriented so as to receive and detect the one or more infrared wavelengths of radiation emitted by radiation source 252 that exit airway adapter 20" through window 42.

Figure 8:
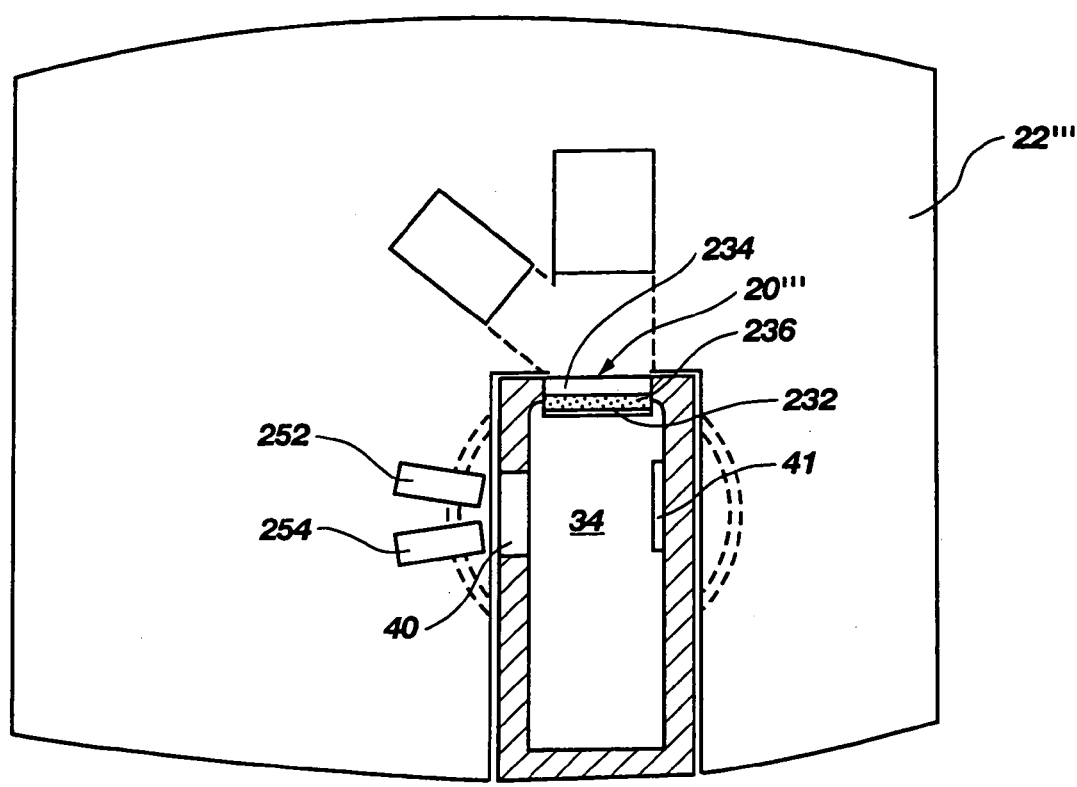
FIG. 8 is a cross-sectional representation of an airway adapter that includes a single window through which a luminescence quenching measurement of one or more substances may be obtained and another single window and corresponding optics through which an infrared measurement of one or more substances may be obtained.

Alternatively, or in combination with other airway adapter features disclosed herein, as depicted in FIG. 8, an airway adapter 20'" incorporating teachings of the present invention includes a single window 40 through which an infrared emitter 252 and infrared detector 254 may be used to measure an amount of a substance, such as carbon dioxide, nitrous oxide or another anesthetic agent, in the respiration of an individual. Window 40 of airway adapter 20''' is positioned on one side of flow passage 34 to facilitate the introduction of one or more infrared wavelengths of radiation into flow passage 34, while optics 41, which reflect or otherwise redirect infrared wavelengths of radiation back across flow passage 34 and through window 40, are positioned at least partially across flow passage 34 from window 40.

Window 40 may be formed from a material that is substantially transparent to (i.e., has a high transmissivity for) infrared wavelengths that are desired for use in measuring amounts of one or more substances in respiration of the individual.

Optics 41 may include one or more mirrors or reflective coatings, as well as other optical components of known types (e.g., lenses, filters, etc.) to direct a beam of radiation that originated from a infrared emitter 252 within transducer housing 22''' and was introduced into flow passage 34 of airway adapter 20''' back across flow passage 34, through window 40, and to an infrared detection component 254 carried by transducer housing 22''', positioned adjacent infrared emitter 252.

As in previously described embodiments, airway adapter 20''' is configured to seat a transducer housing 22''', which carries infrared emitter 252 and infrared detector 254. Upon assembling transducer housing 22''' and airway adapter 20''', infrared emitter 252 is oriented such that infrared emitter 252 is positioned to emit infrared wavelengths of radiation into window 40, at least partially across flow passage 34, toward optics 41. Likewise, upon assembling airway adapter 20''' and transducer housing 22''', infrared detector 254 is oriented so as to receive infrared wavelengths of radiation that have been redirected by optics 41 back out of window 40.

As one or more infrared wavelengths of radiation pass across at least a portion of flow passage 34 adjacent to window 40 and through the respiration of an individual passing through that portion of flow passage 34, each infrared wavelength may be attenuated, or decreased in intensity, to a degree that correlates to an amount of a corresponding substance present in the individual's respiration.

Other exemplary embodiments of airway adapters incorporating teachings of the present invention are depicted in FIGS. 9-12. As shown in FIGS. 9-12, an airway adapter 120 of the present invention may include a single pair of windows 140 and 142 through which both infrared and luminescence quenching measurements may be obtained.

Window 140 is substantially transparent to (i.e., has a high transmissivity for) at least one wavelength of radiation that excites luminescable material 232 into luminescence. In addition, window 140 is substantially transparent to one or more of infrared wavelengths of radiation that are useful for measuring amounts of one or more substances present in respiration or other gas mixtures passing through a location of flow passage 34 positioned between windows 140 and 142.

Window 142 is substantially transparent to the one or more infrared wavelengths of radiation to which window 140 is substantially transparent. Window 142 is also substantially transparent to at least one wavelength of radiation that is emitted by luminescable material 232, the intensity of which decreases at a rate that is indicative of an amount of a measured substance in respiration within flow passage 34.

Figure 9:
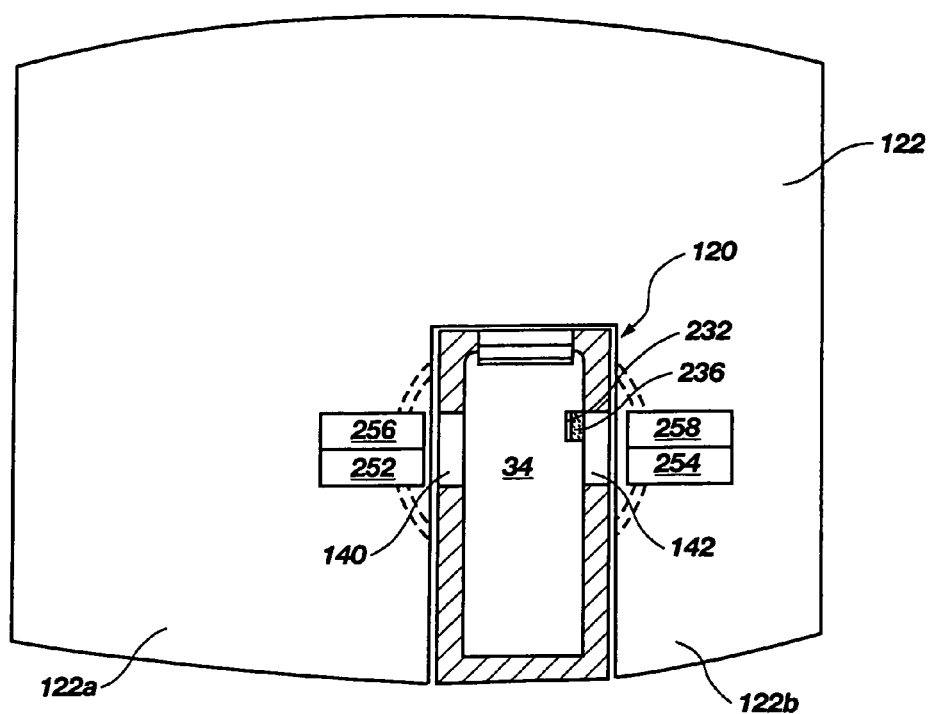
FIGS. 9 and 11 are cross-sectional assembly views of alternative embodiments of airway adapters and transducers according to the present invention, which include pairs of opposed windows through which both luminescence quenching and infrared measurements of one or more substances may be obtained.
Figure 10:
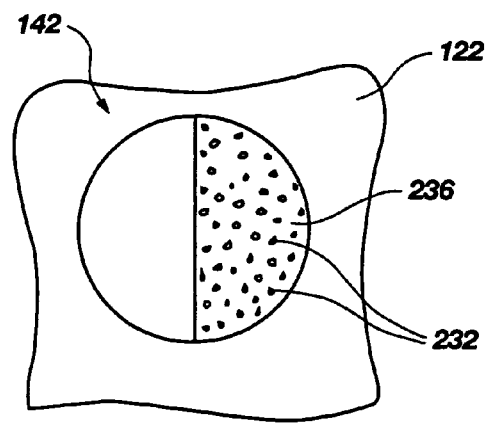
FIGS. 10 and 12 are partial views of airway adapter windows of the airway adapter embodiments depicted in FIGS. 9 and 11, respectively.
Figure 11:
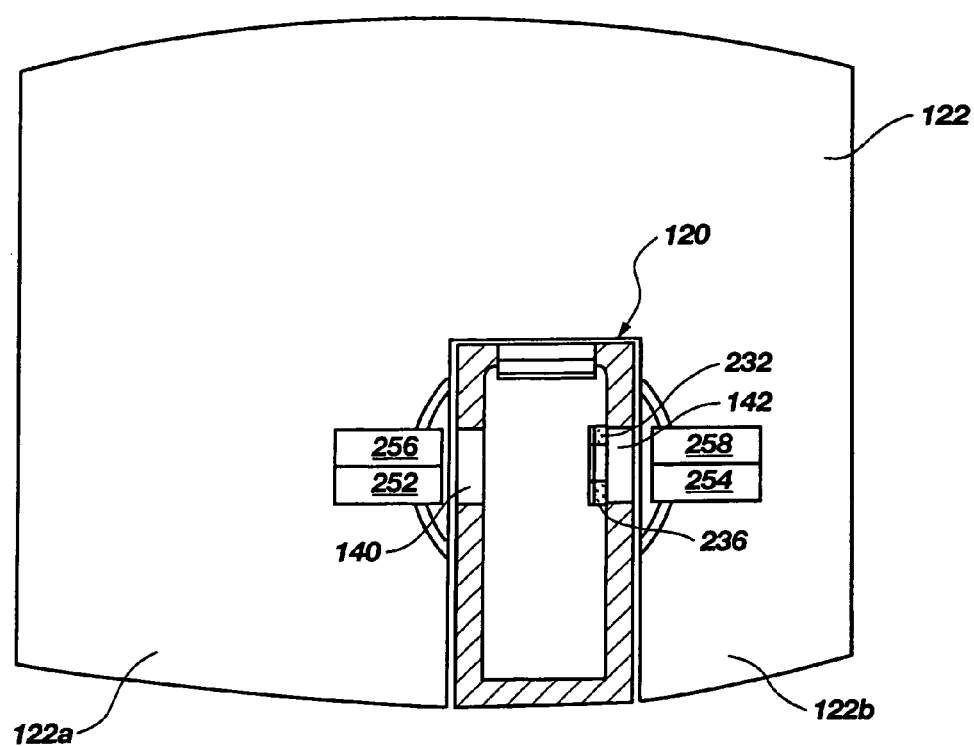
Figure 12:
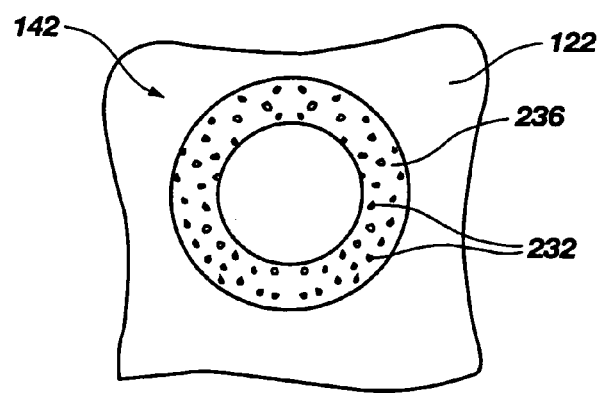

While radiation may pass through any portion of window 140, a membrane 236 carrying luminescable material 232 is positioned adjacent to a portion of window 142. As shown in FIGS. 9 and 10, membrane 236 is semicircular in shape. FIGS. 11 and 12 depict a membrane 236 having an annular shape, and positioned adjacent an outer periphery of window 142. Membranes 236 of other shapes and covering different portions of window 142 are also within the scope of the present invention.

A transducer housing 122 configured complementarily to airway adapter 120 includes two legs 122a and 122b, one of which (first leg 122a) is configured to be positioned adjacent to window 140 and the other of which (second leg 122b) is configured to be positioned adjacent to window 142.

First leg 122a of transducer housing 122 carries infrared emitter 252 and radiation source 256, which emits at least one wavelength of radiation that will excite luminescable material 232. Both infrared emitter 252 and radiation source 256 are positioned to emit their respective wavelengths of radiation into window 140 and through flow passage 34. While infrared emitter 252 is also oriented so as to direct radiation emitted therefrom through an unobstructed (by membrane 236) portion of window 142, radiation source 256 is oriented to direct radiation emitted therefrom toward membrane 236 so as to excite luminescable material 232 carried thereby into luminescence.

As an alternative, membrane 236 may substantially cover window 142 if membrane 236 and luminescable material 232 thereon are substantially transparent to one or more wavelengths of infrared radiation that are used to detect the partial pressure or amount of carbon dioxide or one or more other substances present in respiratory or other gases that are flowing through airway adapter 120.

Second leg 122b of transducer housing 122 carries an infrared detection component 254 and luminescence detector 258. Infrared detection component 254 is positioned to receive and detect one or more infrared wavelengths of radiation exiting airway adapter 120 through window 142. Luminescence detector 258 is oriented to receive and detect one or more wavelengths of radiation that are emitted from luminescable material 232 and that are quenched, or reduced in intensity, to a degree representative of an amount of a monitored substance in respiration to which luminescable material 232 is exposed.

As an alternative to the embodiments illustrated in FIGS. 9 and 11, radiation source 256 may be located within second leg 122b of transducer housing 122 and positioned to direct radiation toward a portion of window 142 adjacent to which membrane 236 with luminescable material 232 thereon is positioned. In another alternative, one or both of luminescence sensor 258 and radiation source 256 could be carried by first leg 122b of transducer housing 122.

Figure 13:
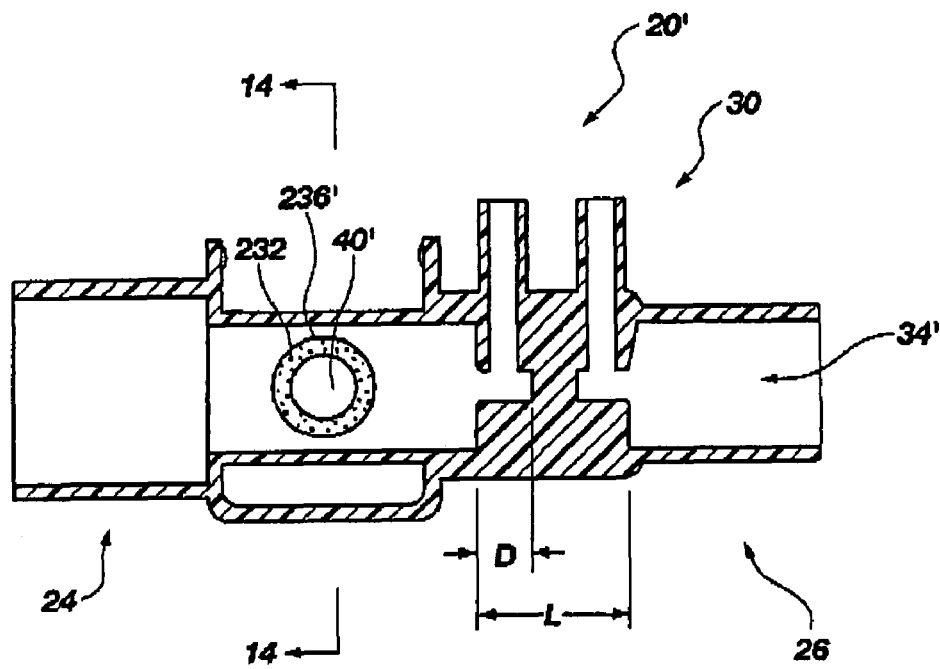
FIG. 13 is a cross-sectional representation of the airway adapter that includes a single window through which both infrared and luminescence quenching measurements may be taken.
Figure 14:
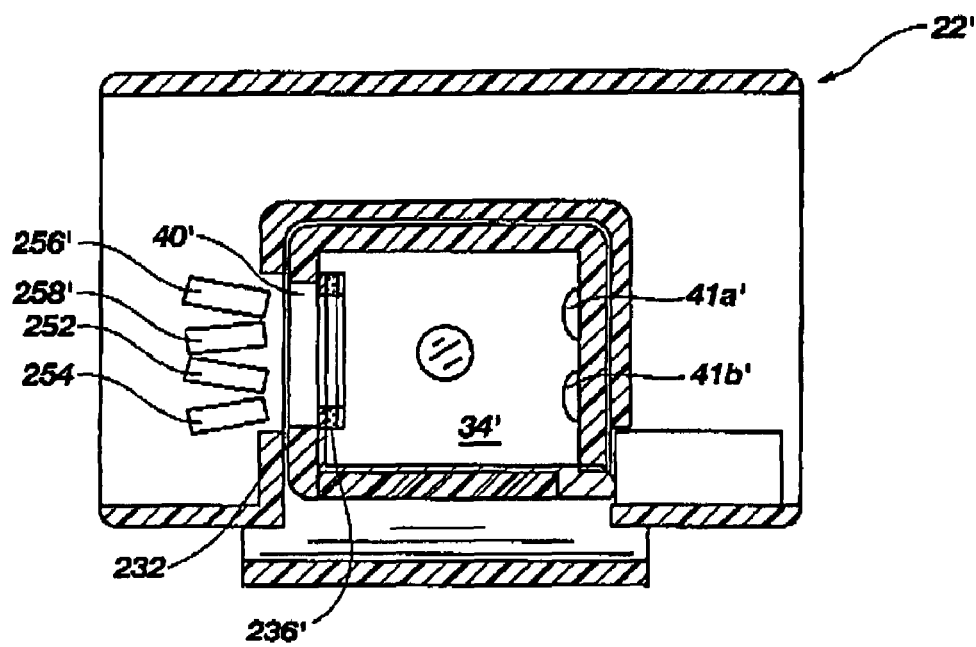
FIG. 14 is a cross-section taken along line 14-14 of FIG. 13, also showing a transducer assembled with the airway adapter.

FIGS. 13 and 14 depict another exemplary embodiment of airway adapter 20' incorporating teachings of the present invention, which includes a single window 40' through which measurements of the amounts of oxygen, carbon dioxide, and anesthetic agents in the respiration of an individual may be obtained. As illustrated, membrane 236', which carries luminescable material 232, is positioned within flow passage 34' on a portion of window 40'. While membrane 236' is depicted as being annular in shape and covering a periphery of window 40', airway adapters with other shapes of membranes are also within the scope of the present invention. Furthermore, the membrane that carries luminescable material 232 need not be positioned on window 40', but may be positioned elsewhere within flow passage 34' or in a location that is in flow communication with flow passage 34'.

Airway adapter 20' also includes one or more mirrors 41a', 41b' (FIG. 14) that are positioned so as to facilitate measurement of the amounts of one or more of oxygen, carbon dioxide, and anesthetic agents in the respiration of an individual through window 40'. As depicted, airway adapter 20' includes mirrors 41a', 41b', which facilitate collection of measurements that are indicative of an amount of carbon dioxide and/or an anesthetic agent in an individual's respiration. By way of example only, each mirror 41' may shaped or positioned within flow passage 34 so as to reflect radiation that has been introduced into flow passage 34 through window 40' and that has traversed at least a portion of the distance across flow passage 34 back through window 40'. Of course, mirror 41' may actually comprise a group of mirrors or other optical elements (e.g., filters, lenses, etc.) or known types to facilitate the direction of radiation of particular wavelengths to the appropriate locations.

As depicted in FIG. 14, a transducer housing 22' that is configured to be assembled with airway adapter 20' includes a radiation source 256' and a corresponding luminescence detector 258'. Radiation source 256' emits at least one wavelength of electromagnetic radiation that will excite luminescable material 232. Radiation source 256' is positioned to introduce one or more wavelengths of excitation radiation through window 40' and onto luminescable material 232. At least a portion of the radiation that is emitted from luminescable material 232 is then received by luminescence detector 258'. Luminescence detector 258' detects at least one wavelength of radiation emitted from luminescable material 232 that indicates an amount of oxygen present in respiration or another gas mixture flowing through flow passage 34.

Transducer housing 22', as shown in FIG. 14, may also carry an infrared radiation emitter 252 and an infrared detector 254. Infrared emitter 252 emits one or more wavelengths of radiation that are useful for detecting an amount of carbon dioxide, an anesthetic agent, or another gas or vaporized material that are present in respiration or another mixture of gases located within flow passage 34'. As shown, infrared emitter 252 is positioned to direct the one or more wavelengths of radiation into window 40', at least partially across flow passage 34', and toward mirror 41a', 41b'. Mirror 41a', 41b' then reflects the one or more wavelengths of radiation back toward a location of window 40' where the radiation will be received or sensed by infrared detector 254.

Of course, one or more lenses may be associated with radiation source 256' and/or luminescence detector 258' to focus radiation being emitted by radiation source 256' or received by luminescence detector 258'. One or more filters may similarly be associated with radiation source 256' to limit the wavelengths of radiation to which luminescable material 232 is exposed. Also, one or more filters may be associated with luminescence detector 258' to restrict the wavelengths of radiation that may be received thereby.

Referring generally to FIGS. 1-5, 13, and 14 airway adapter 20, 20' and transducer housing 22, 22' may be molded from a polycarbonate or a comparable rigid, dimensionally stable polymer. Nonetheless, several factors, including, without limitation, the type of luminescable material 232 being used, as well as wavelengths of radiation that excite luminescable material 232, that are emitted by luminescable material 232, and that are used to detect other substances, such as carbon dioxide or nitrous oxide or other anesthetic agents, may also be taken into consideration when selecting the material or materials that are to be used to form airway adapter 20, 20'. Such factors may also be considered when selecting one or more materials from which transducer housing 22, 22' will be formed.

When an airway adapter 20, 20' incorporating teachings of the present invention includes luminescable material 232, the material or materials from which airway adapter 20, 20' and transducer housing 22, 22' are formed preferably prevent luminescable material 232 from being exposed to wavelengths of ambient light which may excite luminescable material 232 (i.e., the material or materials are opaque to such wavelengths of radiation). Additionally, the material or materials of airway adapter 20, 20' and transducer housing 22, 22' preferably prevent luminescence detector 258 from being exposed to the same wavelengths of ambient radiation that luminescable material 232 emit upon being excited and that are quenched, or reduced in intensity, to a degree that is representative of an amount of oxygen or another analyzed gas or vaporized material to which luminescable material 232 is exposed. One or both of airway adapter 20, 20' and transducer housing 22, 22' may also be equipped with light sealing elements or optical filters that further prevent luminescable material 232 and luminescence detector 258, 258' from being exposed to undesirable wavelengths of ambient radiation.

It is also preferred that the material or materials from which airway adapter 20, 20' and transducer housing 22, 22' are formed do not emit or fluoresce wavelengths of radiation that would either excite luminescable material 232 or be emitted therefrom upon exposure of airway adapter 20, 22' or transducer housing 22, 22' to either ambient radiation or to wavelengths of radiation that are emitted by infrared emitter 252, radiation source 256, 256', or excited luminescable material 232.

Portions of airway adapter 20, 20' or transducer housing 22, 22', such as window 40, through which one or more wavelengths of radiation are to be transmitted are preferably formed from materials that do not absorb a substantial amount of the one or more wavelengths of radiation that are to be transmitted therethrough. Stated another way, these portions of airway adapter 20, 20' or transducer housing 22, 22' should be relatively transparent to the wavelengths of radiation that are indicative of an amount of one or more particular substances in the respiration of a patient. By way of example only and not to limit the use of polypropylene in airway adapter 20, 20' or in transducer housing 22, 22', while polypropylene has a high transmissivity for wavelengths that are used to detect carbon dioxide levels, polypropylene may not have good transmissivity for wavelengths of radiation that may be used to detect levels of other substances.

As discussed above and illustrated in FIGS. 1-5, airway adapter 20 may include a respiratory flow monitoring device 30 within first tubular portion 24 (most clearly seen in FIGS. 4 and 5). Respiratory flow monitoring device 30 of airway adapter 20 may comprise any known, suitable type of respiratory flow monitor. An exemplary respiratory flow monitoring device 30 includes a diametrically-oriented longitudinally-extending strut 44 of axial length L and height H1 within a tubular housing 46 of airway adapter 20. Strut 44 has first and second end faces 50 and 52, and first and second side faces 54 and 56.

It is contemplated that the end faces 50 and 52 may be substantially perpendicular to axis A, as shown in FIG. 5, and chamfered and rounded, as shown, so long as the end face configuration is symmetrical when viewed from above. The major characteristic of end faces 50 and 52, aside from symmetry, is that they do not incline toward notches 58 and 60 or otherwise collect or direct flow through flow monitoring device 30 toward notches 58 and 60 and pressure ports 62 and 66. End faces 50 and 52 are preferably aerodynamically designed so as to minimize resistance to the gas flow.

As shown in FIG. 5, side faces 54 and 56 of strut 44 are flat, again the major requirement being one of symmetry between the sides of strut 44, as with end faces 50 and 52.

Strut 44 also provides a position for pressure port apertures 62 and 66 and conditions the velocity profile of the flowing gas. Strut 44 is offset from an inner wall 48 of tubular housing 46 and is secured, at both ends, to inner wall 48.

The cross-sectional area of the 44 transverse to a bore axis A should be minimized. The minimization of this dimension is, however, constrained by the diameters of pressure port apertures 62 and 66. Typically, the cross sectional area of strut 44 may be about five percent (5%) of the cross-sectional bore area of tubular housing 46 at the location of strut 44.

It should be noted that the diameter of the bore through tubular housing 46, depicted in FIGS. 4-5, is different between first tubular portion 24 and second tubular portion 26. This configuration accommodates a male connecting tube element shown in broken lines and designated as M on the left-hand side or first tubular portion 24 of airway adapter 20, and a female connecting tube element F on the right-hand side of second tubular portion 26 of airway adapter 20. Also, the internal bores of first and second tubular portions 24 and 26 may be tapered to facilitate the release of plastic injection molding mold parts from a formed airway adapter 20.

Strut 44 further includes notch structures comprising substantially symmetrical first and second notches 58 and 60, both of which are located substantially on axis A of tubular housing 46, notches 58 and 60 extending axially inwardly from first and second end faces 50 and 52, respectively, and laterally through first and second side faces 54 and 56, respectively. A first pressure port 62 of a first lumen 64 opens into first notch 58, and a second pressure port 66 of a second lumen 68 opens into second notch 60, first and second lumens 64 and 68 comprise passages internal to strut 44, which extend into and through first and second male stems 70 and 72, respectively, on exterior surface 74 of tubular housing 46.

Airway adapter 20 is preferably oriented with first and second male stems 70 and 72 directed upward, such that water condensation and mucus do not clog or otherwise impair pressure ports 62 and 66.

Both pressure ports 62 and 66 face substantially perpendicular to axis A of tubular housing 46, notches 58 and 60 extend axially inwardly to a depth D, at least past pressure ports 62 and 66, and may so extend a distance equal to the height H2 of notches 58 and 60, which, in turn, should be less than or equal to four-tenths (4/10) of the height H1 of the strut 44.

Back walls 78 and 80 of notches 58 and 60, respectively, may be arcuate or radiused, as shown in FIG. 5, or otherwise symmetrically shaped, as with the end faces 50 and 52. Back walls 78 and 80 may also have substantially planar surfaces.

Floors 82 and 84 and ceilings 86 and 88 of notches 58 and 60, respectively, are preferably substantially planar, or flat, as shown in FIG. 4, or may be otherwise symmetrically shaped. Likewise, the transition edges or lines between end faces 50 and 52 and notches 58 and 60 are preferably radiused, although they may alternatively be chamfered or beveled.

Back walls 78 and 80 of notches 58 and 60, respectively, together with restrictions (ridges or lands) 90 comprise an obstruction 76 and/or perturbation to the gas flow through flow monitoring device 30, which generates the differential pressure signal measured at first and second pressure ports 62 and 66. The measured differential pressure signal is from either pressure loss or from vena contracta, the contraction of the velocity profile of flowing gases, which is caused by obstruction 76. The differential pressure generated from the vena contracta can be modeled by standard fluid mechanics equations such as Euler's or Bernoulli's equation. The differential pressure signal generated from vena contracta is considered "lossless", meaning that the pressure is restored as the velocity profile is returned to the incident velocity profile.

Respiratory flow, as measured by flow monitoring device 30, is proportional to the square root of the differential pressure, as measured at pressure ports 62 and 66.

Flow obstruction 76 may be varied in a number of ways to yield a different magnitude of measured differential pressure for a given flow rate. First, the cross-sectional area of restrictions (ridges or lands) 90 may be increased or decreased in the plane perpendicular to axis A. Also, the distance from the center of first pressure port 62 to back wall 78 of notch 58 and, likewise, the distance from the center of the second pressure port 66 to back wall 84 of notch 60, may be varied to change the flow response characteristics. The magnitude of the differential pressure signal for a given flow rate can be further increased by reducing the cross-sectional bore area by necking down the inner wall of tubular housing 46.

The length and width of strut 44 may be altered, as desired, to change flow characteristics. These flow characteristics include flow conditioning, signal strength, and signal stability. Ideally, the incident velocity profile to the obstruction should be the same regardless of the velocity profile incident to airway adapter 20. Signal stability may be compromised when unstable, multi-dimensional vortex formations are generated by flow obstruction 76. Strut 44 with notch means provides flow conditioning that yields some immunity to inlet velocity profile and yields a stable differential pressure signal in response to the gas flow.

Flow monitoring device 30 may be selectively modified to adapt to the conditions under which flow monitoring device 30 is to operate. In particular, the modification of the cross-sectional flow area in the vicinity of strut 44 may be employed to adjust the dynamic range of the respiratory flow monitoring device 30, as may modifications to the configurations of end faces 50 and 52, back walls 78 and 80 of notches 58 and 60, and to the lines of transition between notches 58 and 60 and end faces 50 and 52 and side faces 54 and 56. It is preferred to use laterally extending transversely oriented center (strut 44) restrictions (ridges or lands) 90 and a gradual inner wall transition in the strut area axial length to add symmetry to the flow pattern, normalize the flow, immunity to moisture, and provide better repeatability of readings. The notch height H2 or the length of strut 44 may be increased or decreased to accommodate a wider range of inlet conditions, such as might result from employment of flow monitoring device 30 with a variety of endotracheal tubes.

Figure 15:
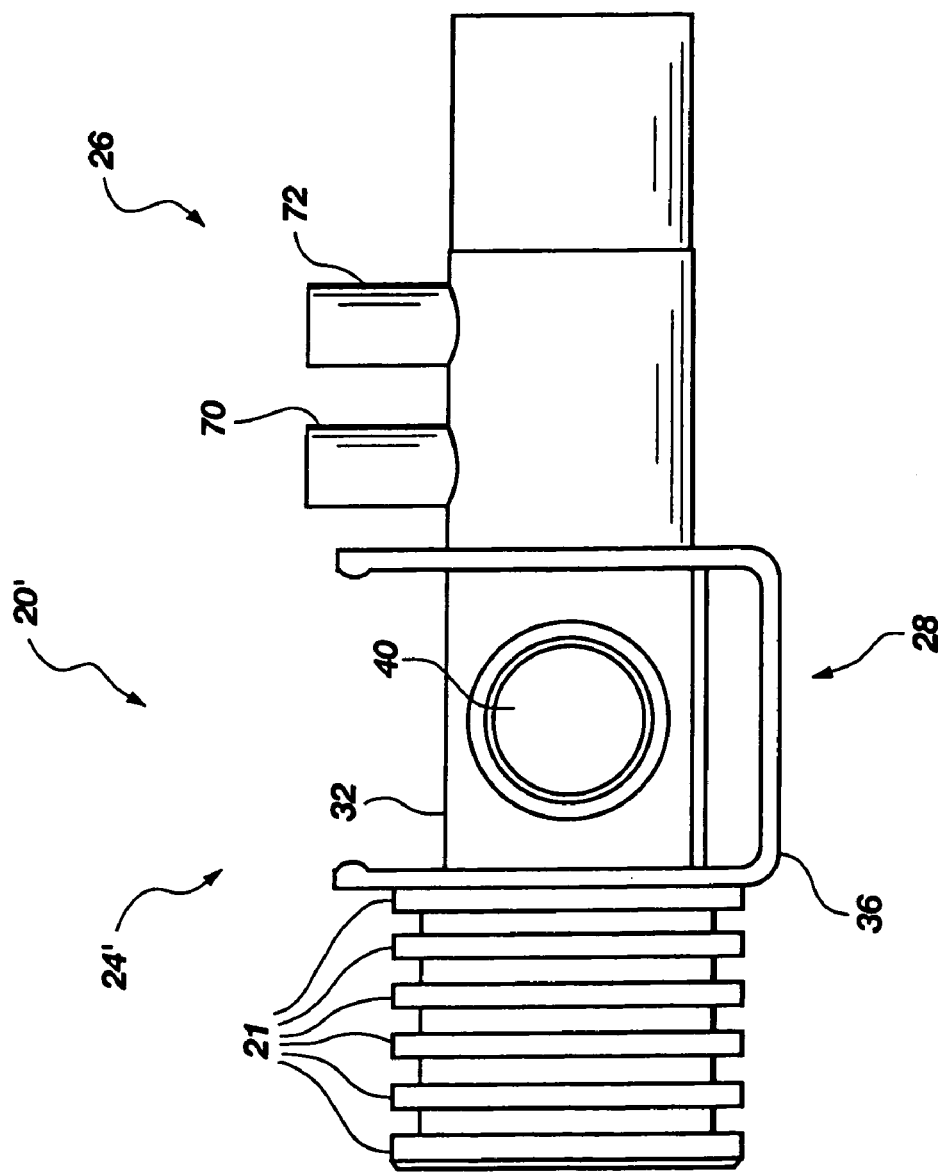
FIG. 15 is a side elevation view of a second preferred embodiment of the airway adapter of the present invention.

FIG. 15 illustrates a second embodiment of airway adapter 20' incorporating teachings of the present invention. Airway adapter 20' includes a plurality of ribs 21 around the outside diameter of a first portion 24' thereof. Ribs 92 preferably define a 22 mm diameter and reduce the weight of airway adapter 20' while providing uniform wall dimensions to facilitate injection molding of airway adapter 20'.

Figure 16:
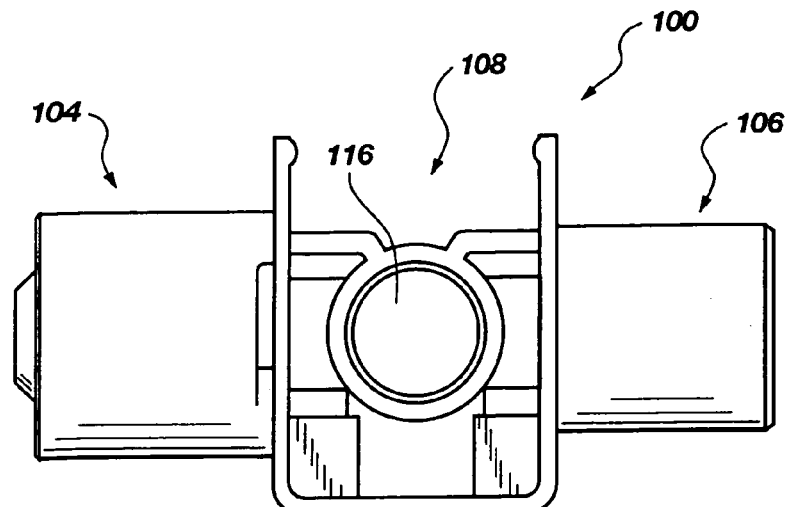
FIG. 16 is a side elevation view of a third preferred embodiment of the airway adapter of the present invention.
Figure 17:
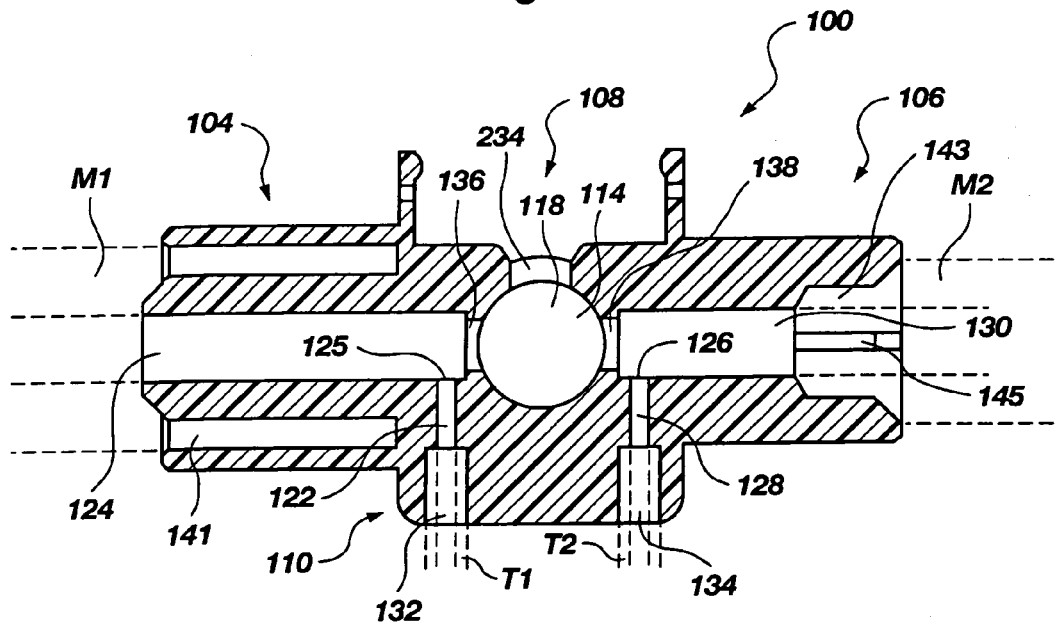
FIG. 17 is a side sectional elevation of the airway adapter of FIG. 16.
Figure 18:
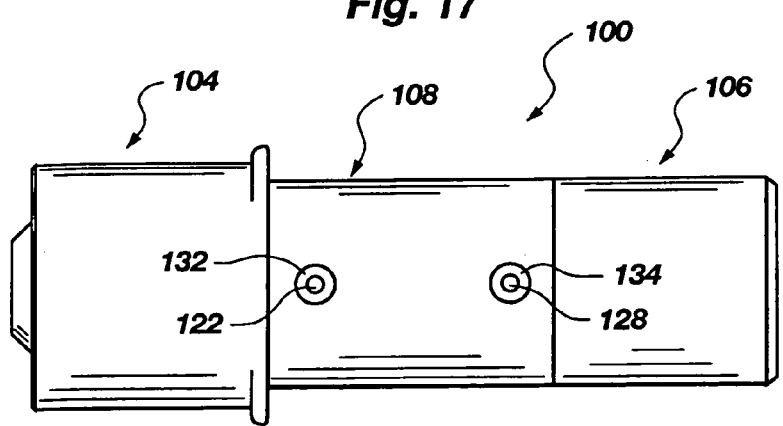
FIG. 18 is a bottom view of the airway adapter of FIG. 16.
Figure 19:
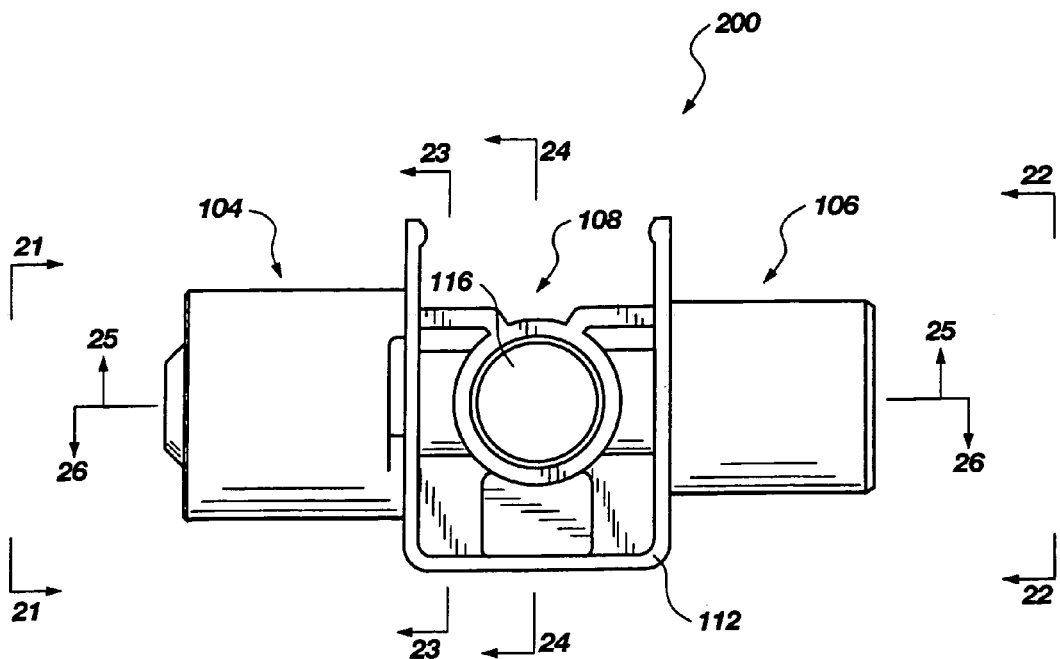
FIG. 19 is a side elevation view of a fourth preferred embodiment of the airway adapter of the present invention.
Figure 20:
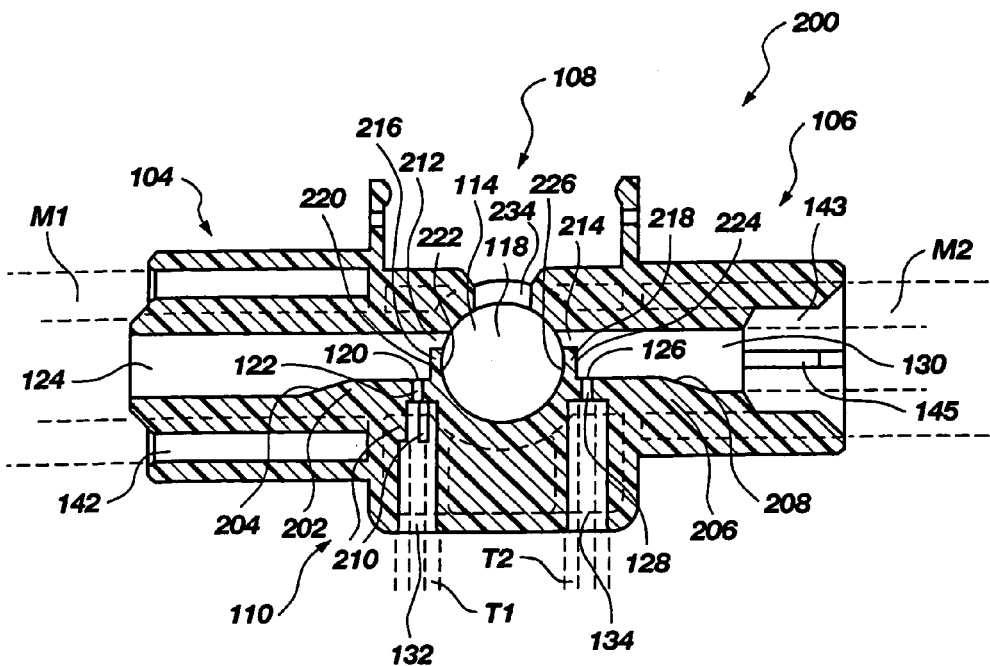
FIG. 20 is a side sectional elevation of the airway adapter of FIG. 19.
Figure 21:
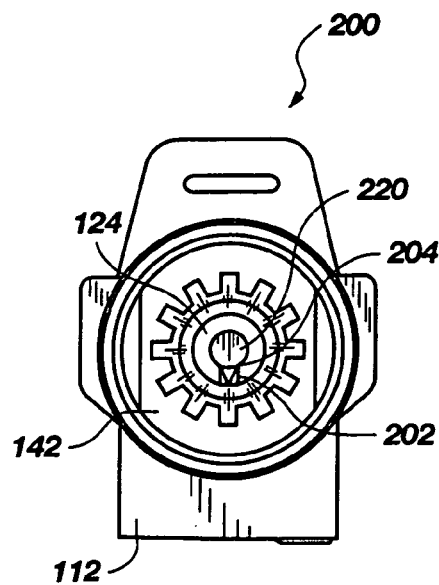
FIG. 21 is an end elevation view of the airway adapter along lines 21-21 of FIG. 19.
Figure 22:
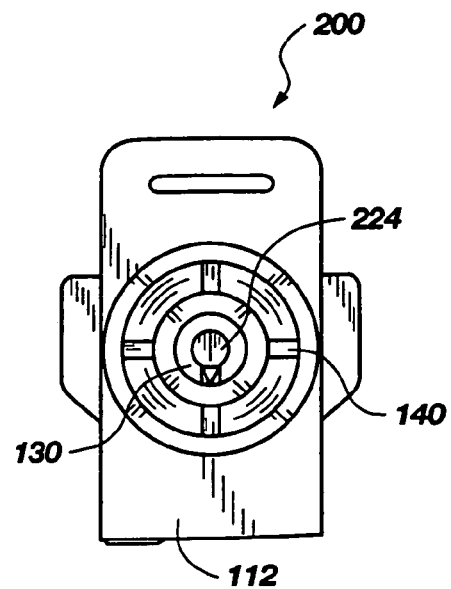
FIG. 22 is an end elevation view of the airway adapter along lines 22-22 of FIG. 19.
Figure 23:
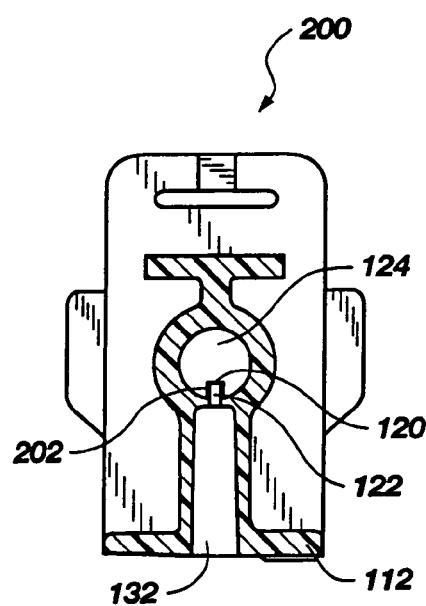
FIG. 23 is a sectional view of the airway adapter of FIG. 19, looking from plane 23-23.
Figure 24:
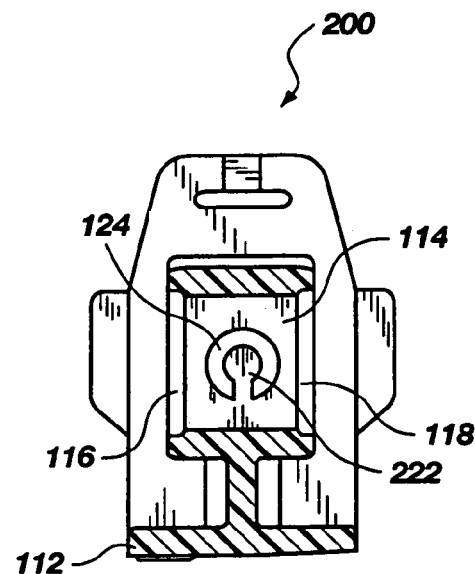
FIG. 24 is a sectional view of the airway adapter of FIG. 19, looking from plane 24-24.
Figure 25:
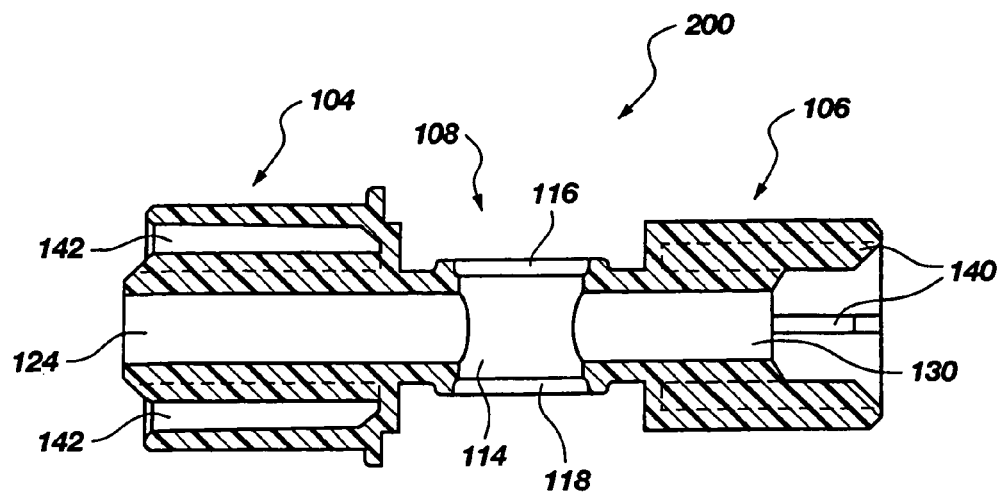
FIG. 25 is a sectional view of the airway adapter of FIG. 19, looking from plane 25-25.
Figure 26:
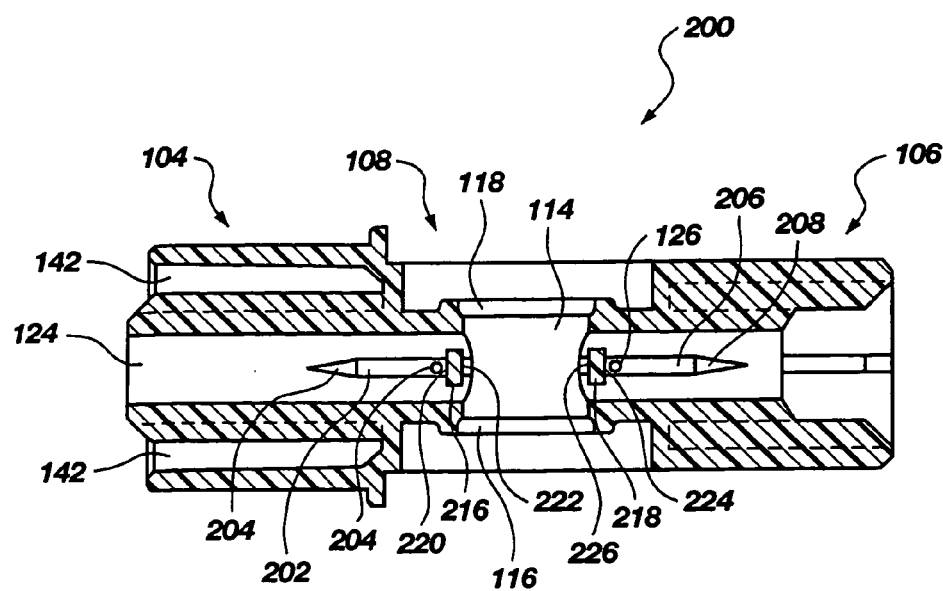
FIG. 26 is a sectional view of the airway adapter of FIG. 19, looking from plane 26-26.

FIGS. 16-18 illustrate third embodiment of an airway adapter 100 with reduced dead space relative to the embodiments disclosed previously herein. Airway adapter 100 is particularly suitable for use in situations where the respiratory tidal volume is extremely small, such as with newborn infants, although airway adapter 100 has equal utility in adult and pediatric respiratory monitoring.

As shown, airway adapter 100 is designed for connection between a patient ventilation device, such as an endotracheal tube inserted into a patient's trachea, attached to a first tubular portion 104 of airway adapter 100, and the tubing of a mechanical ventilator, attached at second tubular portion 106 of airway adapter 100. First and second tubular portions 104 and 106 have bores of varying diameter and of substantially circular cross-section. As shown in FIGS. 16-18, a gas concentration monitoring portion 108 of airway adapter 100 is disposed between first and second tubular portions 104 and 106.

Gas concentration monitoring portion 108 of airway adapter 100 provides a seat for a transducer housing (not shown), similar to transducer housing 22 shown in FIG. 1. An integral, U-shaped casing element 112 positively locates the transducer housing into position on airway adapter 100. In a preferred embodiment, the transducer housing snaps into place on airway adapter 100 without the need for tools to assemble or disassemble the transducer and airway adapter 100.

As illustrated, airway adapter 100 includes an annular recess 141 formed in first portion 104. Annular recess 141 accommodates a male connecting tube element, shown in broken lines and designated as M1, on the left-hand side of first portion 104 of airway adapter 100. Second tubular portion 106 similarly includes a receptacle 143 configured to accommodate a second male connecting tube element M2, as shown in broken lines, which snaps into receptacle 143 by engaging a stepped slot 145 thereof. Elements M1 and M2 each include a bore of like diameter to the corresponding bores 130 and 124 of airway adapter 100. Elements M1 and M2 facilitate communication between airway adapter 100 and the airway of an individual and, if necessary, a respirator or other ventilation device.

Gas concentration monitoring portion 108 includes a luminescent sensing window 234 formed through U-shaped casing element 112. Window 234 facilitates the emission of excitation radiation from a source of excitation radiation within a transducer housing assembled with airway adapter 100, into airway adapter 100, and toward luminescable material (e.g., luminescable material 232 shown in FIG. 4) within airway adapter 100. In addition, window 234 facilitates the detection of luminescence emitted from the luminescable material of airway adapter 100 by a detector within the transducer housing, as discussed previously herein with reference to FIG. 6.

Gas concentration monitoring portion 108 also includes a first axially aligned window 116 and a second axially aligned window 118 (shown in FIG. 17 only) to allow an infrared radiation beam to travel from an infrared radiation emitter (see FIG. 1) in the transducer housing transversely through a sampling chamber 114 in airway adapter 100 for monitoring gases, such as $CO_2$, $N_2O$, and anesthetic agents, as discussed previously herein.

Airway adapter 100 includes a respiratory flow monitoring device 110, which partially resides in first tubular portion 104, partially resides in second tubular portion 106, and partially resides in gas concentration monitoring portion 108.

Respiratory flow monitoring device 110, which is most clearly depicted in FIG. 17, also includes a first pressure port 125 of a first lumen 122 which opens into a first tubular chamber 124 of the tubular portion 104, and a second pressure port 126 of a lumen 128 which opens into second tubular chamber 130. Lumens 122 and 128 extend to respective first and second recesses 132, 134, which are configured to minimize dead space and accommodate connecting tubes, shown in broken lines and designated as T1 and T2. Tubes T1 and T2 are connected to a flow monitor (not shown), which determines flow rate through a pressure differential detected between pressure ports 125 and 126. This pressure differential is produced through the use of necked-down ports 136 and 138 at the longitudinal ends of gas sampling chamber 114.

The heat generated by the radiation sources 252, 256 of transducer housing 22 (FIGS. 1, and 6) or from one or more other sources, which may be placed over airway adapter 100, should help to reduce the tendency of breath moisture to condense in airway adapter 100. The effects of water condensation are of particular concern in this embodiment due to its small volume and intended neonatal use, therefore, the airway adapter 100 should be positioned such that recesses 132 and 134 are directed upward to prevent clogging.

It has been found that this embodiment has many advantages, such as minimization of deadspace and moldability in one piece.

FIGS. 19-26 illustrate a fourth preferred embodiment of an airway adapter 200, which is similar to the airway adapter 100 of FIGS. 16-18. Therefore, components common to airway adapters 100 and 200, depicted in FIGS. 16-18 and FIGS. 19-26, respectively, retain the same numeric designation. Airway adapter 200 is particularly suitable for use in situations where the respiratory tidal volumes is extremely small, such as with newborn infants, although it has equal utility in pediatric and adult respiratory monitoring.

Airway adapter 200 is designed for connection between a patient ventilation device, such as an endotracheal tube inserted in a patient's trachea, attached to the first tubular portion 104, and the tubing of a mechanical ventilator, attached at second tubular portion 106. First and second tubular portions 104 and 106 have bores of varying diameter and of substantially circular cross-section, with gas concentration monitoring portion 108 positioned therebetween.

Gas concentration monitoring portion 108 of airway adapter 200 provides a seat for a transducer housing (not shown), similar to transducer housing 22 shown in FIG. 1. An integral, U-shaped casing element 112 positively locates the transducer housing into position on airway adapter 200. Preferably, the transducer housing snaps into place on airway adapter 200 without the need for tools to assemble or disassemble airway adapter 200 and the transducer housing.

In this embodiment, as with the embodiment of FIGS. 16-18, an annular recess 142 is formed in first portion 104 to accommodate a male connecting tube element, shown in broken lines and designated as M1, on the left-hand side of first portion 104 of airway adapter 200. Second tubular portion 106 includes a receptacle 143 that accommodates a second male connecting tube element M2, as shown in broken lines, which snaps into receptacle 143 by engaging a stepped slot 145 thereof. Elements M1 and M2 include bores of like diameter to bores 124, 130. Elements M1 and M2 facilitate communication between airway adapter 200 and the airway of an individual and, if necessary, a respirator or other ventilation device.

Gas concentration monitoring portion 108 includes a luminescent sensing window 234 formed through U-shaped casing element 112. Window 234 facilitates the emission of excitation radiation from a source of excitation radiation within a transducer housing assembled with airway adapter 200, into airway adapter 200 toward luminescable material (e.g., luminescable material 232 shown in FIG. 4) within airway adapter 200. In addition, window 234 facilitates the detection of luminescence emitted from the luminescable material of airway adapter 200 by luminescence detector 258 within transducer housing 22, as discussed previously herein with reference to FIG. 6.

Gas concentration monitoring portion 108 also includes a first axially aligned window 116 and a second axially aligned window 116 and a second axially aligned window 118 to facilitate the transmittance of an infrared radiation beam from an infrared radiation emitter in the transducer housing, transversely through sampling chamber 114 in airway adapter 200 so that amounts of gases, such as $CO_2$, $N_2O$, and anesthetic agents in the respiration of an individual may be monitored as discussed previously herein.

Airway adapter 200 includes a respiratory flow monitoring device 110, which partially resides in first tubular portion 104, partially resides in second tubular portion 106, and partially resides in gas concentration monitoring portion 108. Respiratory flow monitoring device 110 includes a first pressure port 120 of a first lumen 122 that extends through a first strut 202 and opens into a first tubular chamber 124 of a first tubular portion 104. First strut 202 has a tapered portion 204 directed toward first tubular portion 104 to minimize potential flow disturbances. Respiratory flow monitoring device 110 also includes a second pressure port 126 of a second lumen 128 that extends through a second strut 206 and opens into second tubular chamber 130. Second strut 206 has a tapered portion 208 directed toward second tubular portion 106 to minimize potential flow disturbances. Lumens 122 and 128 extend respectively to first and second recesses 132, 134.

Recesses 132 and 134 are configured to minimize dead space and to accommodate male connecting tubes, shown in broken lines and designated as T1 and T2. Recesses 132 and 134 may have internal ribs 210 to securely grip tubes T1 and T2. Tubes T1 and T2 are connected to a flow monitor (not shown), which determines flow rate through a pressure differential detected between pressure ports 120 and 126. This pressure differential is produced through the use of a first annular port 212 and a second annular port 214 at the longitudinal ends of gas sampling chamber 114. First annular port 212 is formed by a first restriction member 216 extending from first strut 202 and blocking a portion of first tubular chamber 124 of first tubular portion 104. The face surfaces 220, 222 of first restriction member 216 are preferably substantially perpendicular to the flow of the respiratory gas through airway adapter 200. Second annular port 214 is formed by a second restriction member 218 extending from second strut 206 and blocking a portion of second tubular chamber 130 of second tubular portion 106. Face surfaces 224, 226 of second restriction member 218 are preferably substantially perpendicular to the flow of the respiratory gas through the airway adapter 200. First restriction member 216 and second restriction member 218 can be any shape, such a circular, oval, rectangular, or the like. However, the preferred shape is a planar disk.

The heat generated by the radiation sources 252, 256 of transducer housing 22 (FIGS. 1, and 6) or from one or more other sources, which may be placed over airway adapter 200, should help to reduce the tendency of breath moisture to condense in airway adapter 200. The effects of water condensation are of particular concern in this embodiment due to its small volume and intended neonatal use, therefore, the airway adapter 200 should be positioned such that recesses 132 and 134 are directed upward to prevent clogging.

It has been found that this embodiment has many advantages, such as minimization of dead space and moldability in one piece.

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. An airway adapter configured to substantially simultaneously provide data indicative of respiratory gas flow and of a concentration of at least two substances present in respiration of an individual, comprising:
   a housing with a bore formed therethough;
   a respiratory flow detection component formed in the housing and in communications with the bore;
   a first respiratory detection component configured to facilitate sensing of at least a first of the at least two substances without diverting respiratory gases from the housing and comprising a detection chamber within the housing, a boundary of the detection chamber at least partially defined by at least one window; and
   a second respiratory detection component disposed on at least a portion of the at least one window and comprising at least one luminescence quenching sensor configured to facilitate sensing of at least a second of the at least two substances without diverting respiratory gases from the housing.

2. The airway adapter of claim 1, wherein the respiratory flow detection component comprises:
   a structure within said housing for creating therein a pressure differential in respiratory gas flow; and
   first and second pressure bores formed in the housing and located so as to facilitate detection of the pressure differential.

3. The airway adapter of claim 2, wherein the structure for creating the pressure differential comprises at least one strut.

4. The airway adapter of claim 3, wherein the first and second pressure bores are at least partially formed within the at least one strut.

5. The airway adapter of claim 4, wherein said at least one strut comprises a restriction member with at least one surface oriented so as to substantially perpendicularly face a direction of respiratory gas flow through the housing.

6. The airway adapter of claim 5, wherein the restriction member has a disk shape.

7. The airway adapter of claim 5, wherein the at least one strut includes a taper oriented toward the detection chamber.

8. The airway adapter of claim 4, wherein said at least one strut is diametrically disposed and longitudinally extends within said bore.

9. The airway adapter of claim 8, wherein the first and second pressure bores communicate respectively with laterally spaced first and second notches formed in the at least one strut proximate a longitudinal axis of the housing.

10. The airway adapter of claim 9, wherein the first and second notches are oriented substantially perpendicularly relative to a length of the at least one strut.

11. The airway adapter of claim 1, wherein the boundary of the detection chamber is at least partially defined by opposed windows.

12. The airway adapter of claim 1, wherein the at least one window is optically compatible so as to permit a beam of infrared radiation to traverse the detection chamber.

13. The airway adapter of claim 1, wherein the first respiratory detection component is configured to facilitate measurement of at least one of $CO_2$, $N_2O$, and an anesthetic agent.

14. The airway adapter of claim 1, wherein the first respiratory detection component and the second respiratory detection component include at least one common element.

15. The airway adapter of claim 1, wherein the at least one window is formed from a polymer.

16. The airway adapter of claim 15, wherein the polymer comprises a biaxially oriented polypropylene.

17. The airway adapter of claim 1, wherein the respiratory flow detection component comprises first and second pressurization ports positioned on opposite sides of the detection chamber.

18. The airway adapter of claim 1, wherein the respiratory flow detection component comprises first and second pressurization ports formed in the housing on the same side of the detection chamber.

19. A respiratory monitoring system, comprising:
   an airway adapter, comprising:
      a housing with a flow passage extending therethough;
      a first window positioned on top of the housing for facilitating luminescence quenching measurements of at least one substance within the flow passage;
   a luminescable material disposed in communication with the flow passage and adjacent the first window;
   a pair of second windows positioned on sides of the housing on opposite sides of the flow passage for facilitating infrared measurements of at least another substance within the flow passage; and
   a transducer-orienting element; and
   a transducer, comprising:
      an attachment feature configured to secure the transducer to the airway adapter, with the transducer-orienting element of the airway adapter defining an orientation of the transducer and a plurality of features thereof with the airway adapter such that luminescence quenching measurements are made through the first window and infrared measurements are made through the second windows.

20. The respiratory monitoring system of claim 19, wherein a membrane carrying the luminescable material is disposed on an inside of the first window.

21. The respiratory monitoring system of claim 19, wherein the transducer-orienting element is configured to orient a radiation source and luminescence detector of the transducer toward the first window, an infrared source of the transducer toward one second window of the pair, and an infrared detection component of the transducer toward another second window of the pair.

22. The respiratory monitoring system of claim 19, further comprising a respiratory flow detection component located along another position of the flow passage than positions of the first window and the pair of second windows.

23. A respiratory monitoring system, comprising: an airway adapter, comprising:
   a housing including:
      a flow passage extending through at least a portion of a length thereof; and
      a transducer orienting element comprising seat for receiving a complementarily configured portion of a transducer;
   a transducer comprising:
      a radiation source and a luminescence detector to make luminescence quenching measurement;
      an infrared source and an infrared detector to make additional measurements;
   a first window in the housing for facilitating luminescence quenching measurements of at least one substance in the flow passage the seat of the housing orienting the radiation source and the luminescence detector of the transducer toward the first window;
   a luminescence material disposed in communications with the flow passage and adjacent the first window;
   a second window in the housing for facilitating infrared measurements of at least another substances in the flow passage the seat of the housing orienting the infrared source and the infrared detection component of the transducer toward the second window; and
   an attachment feature that secures the transducer to the transducer-orienting element of the airways adapter, with the transducer-orienting element defining an orientation of the transducer and a plurality of features thereof with the airway adapter.

24. The respiratory monitoring system of claim 23, wherein a membrane carrying the luminescable material is disposed on an inside of the first window.

25. The respiratory monitoring system of claim 23, wherein the first window is positioned on a top of the housing.

26. The respiratory monitoring system of claim 23, wherein the second window is positioned on a side of the housing.

27. The respiratory monitoring system of claim 23, further comprising a respiratory flow detection component located along another position of the flow passage than positions of the first window and the pair of second windows.

28. A respiratory monitoring system, comprising:
   an airway adapter, comprising:
   a housing with flow passage extending therethough, the housing including:
      a transducer-orienting element comprising a seat that receives a complementarily configured portion of a transducer;
      a first window in the housing for facilitating luminescence quenching measurements of at least one substance within the flow passage a luminescence material disposed in communication with the flow passage and adjacent the first window;
   a pair of second windows positioned in the housing on opposite sides of the flow passage for facilitating infrared measurements of at least another substance within the flow passage;
   a transducer, comprising:
      a radiation source and a luminescence detector for making luminescence quenching measurements;
      an infrared source and an infrared detector for making additional measurements; and
   an attachment feature securing the transducer to the transducer-orienting element, with the seat of the transducer-orienting element of the airway adapter defining an orientation of the transducer and orienting:
the radiation source and the luminescence detector toward the first window;
the infrared source toward one second window of the pair, and the infrared detection component of the transducer toward another second window of the pair.

29. The airway adapter of claim 28, wherein a membrane carrying the luminescence material is disposed on an inside of the first window.

30. The airway adapter of claim 28, further comprising a respiratory flow detection component located along another position of the flow passage than positions of the first window and the pair of second windows.

31. A respiratory monitoring system, comprising: an airway adapter, comprising:
housing including a flow a passage extending through at least a portion of a length thereof;
a first window positioned on top of the housing for facilitating luminescence quenching measurements of at least one substance in the flow passage
a luminescence material disposed in communication with the flow passage and adjacent the first window;
a second window positioned on a side of the housing for facilitating infrared measurements of at least another substance in the flow passage;
a transducer-orienting element;
a transducer_comprising:
a first device for making luminescence quenching measurements through the first window;
a second device for making infrared measurements through the second window;
and an attachment feature securing the transducer to the transducer-orienting element of the airway adapter, with the transducer-orienting element defining an orientation of the transducer and a plurality of features thereof with the airway adapter.

32. The airway adapter of claim 31, wherein a membrane carrying the luminescence material is disposed on an inside of the first window.

33. The airway adapter of claim 31, further comprising:
a respiratory flow detection component located along another position of the flow passage than positions of the first window and the pair of second windows.

34. An airway adapter configured to substantially simultaneously provide data indicative of respiratory gas flow and of concentration of at least two substances present in respiration of an individual, comprising:
a housing with a bore formed therethough and a detection chamber positioned along the bore;
a respiratory flow detection component formed in the housing, in communication with a bore, and comprising first and second pressurization ports positioned on opposite sides of the detection chamber;
a first respiratory detection component configured to facilitate sensing of at least a first of the at least two substances without diverting respiratory gases from the housing and comprising the detection chamber, a boundary of the detection chamber at least partially defined by at least one window, and
a second respiratory detection component comprising at least one luminescence quenching sensor configured to facilitate sensing of at least a second of the at least two substances without diverting respiratory gases from the housing.

35. The airway adapter of claim 34, wherein the respiratory flow detection component comprises:
a structure within the housing for creating therein a pressure differential in respiratory gas flow; and
first and second pressure bores formed in the housing and located so as to facilitate detection of the pressure differential.

36. The airway adapter of claim 35, wherein the structure for creating the pressure differential comprises at least one strut.

37. The airway adapter of claim 36, wherein the first and second pressure bores are at least partially formed within the at least one strut.

38. The airway adapter of claim 37, wherein the at least one strut comprises a restriction member with at least one surface oriented so as to substantially perpendicularly face a direction of respiratory gas flow through the housing.

39. The airway adapter of claim 38, wherein the restriction member has a disk shape.

40. The airway adapter of claim 38, wherein the at least one strut includes a taper oriented toward the detection chamber.

41. The airway adapter of claim 37, wherein the at least one strut is diametrically disposed and longitudinally extends within the bore.

42. The airway adapter of claim 41, wherein the first and second pressure bores communicate respectively with laterally spaced first and second notches formed in the at least one strut proximate a longitudinal axis of the housing.

43. The airway adapter of claim 42, wherein the first and second notches are oriented substantially perpendicularly relative to a length of the at least one strut.

44. The airway adapter of claim 34, wherein the boundary of the detection chamber is at least partially defined by opposed windows.

45. The airway adapter of claim 34, wherein the at least one window is optically compatible so as to permit a beam of infrared radiation to traverse the detection chamber.

46. The airway adapter of claim 34, wherein the first respiratory detection component is configured to facilitate measurement of at least one of $CO_2$, $N_2O$, and an anesthetic agent.

47. The airway adapter of claim 34, wherein the first respiratory detection component and the second respiratory detection component include at least one common element.

48. The airway adapter of claim 34, wherein the at least one window is formed from a polymer.

49. The airway adapter of claim 48, wherein the polymer comprises a biaxially oriented polypropylene.

50. The airway adapter of claim 34, wherein the respiratory flow detection component comprises first and second pressurization ports positioned on opposite sides of the detection chamber.

51. The airway adapter of claim 34, wherein the respiratory flow detection component comprises first and second pressurization ports formed in the housing on the same side of the detection chamber.

* * * * *

UNITED STATES PATENT AND TRADEMARK OFFICE
CERTIFICATE OF CORRECTION

| | | |
|---|---|---|
| PATENT NO. | : 7,335,164 B2 | Page 1 of 1 |
| APPLICATION NO. | : 09/841451 | |
| DATED | : February 26, 2008 | |
| INVENTOR(S) | : Leslie E. Mace et al. | |

It is certified that error appears in the above-identified patent and that said Letters Patent is hereby corrected as shown below:

On the title page:
In ITEM (56) References Cited
Page 2      change "4,652,143 A    3/1987 Wickersheim et al." to --4,652,143 A 5/1987 Wickersheim et al.--

| | | | |
|---|---|---|---|
| CLAIM 2, | COLUMN 24, | LINE 45, | change "said" to --the- |
| CLAIM 5, | COLUMN 24, | LINE 55, | change "said" to --the-- |
| CLAIM 8, | COLUMN 24, | LINE 63, | change "said" to --the-- |
| CLAIM 31, | COLUMN 27, | LINE 29, | change "transducer_comprising" to --transducer comprising-- |

Signed and Sealed this

First Day of September, 2009

David J. Kappos
*Director of the United States Patent and Trademark Office*